United States Patent
Keene et al.

(10) Patent No.: US 6,635,422 B2
(45) Date of Patent: Oct. 21, 2003

(54) METHODS FOR ISOLATING AND CHARACTERIZING ENDOGENOUS MRNA-PROTEIN (MRNP) COMPLEXES

(75) Inventors: Jack D. Keene, Durham, NC (US); Scott A. Tenenbaum, Durham, NC (US); Craig C. Carson, Durham, NC (US)

(73) Assignee: Ribonomics, Inc., Research Triangle Park, NC (US)

( * ) Notice: Subject to any disclaimer, the term of this patent is extended or adjusted under 35 U.S.C. 154(b) by 13 days.

(21) Appl. No.: 09/750,401

(22) Filed: Dec. 28, 2000

(65) Prior Publication Data

US 2002/0004211 A1 Jan. 10, 2002

Related U.S. Application Data

(60) Provisional application No. 60/173,338, filed on Dec. 28, 1999.

(51) Int. Cl.$^7$ .......................... C12Q 1/68; G01N 33/83; C12P 21/06; C12N 15/00; C07H 21/02

(52) U.S. Cl. .......................... 435/6; 435/7.1; 435/7.21; 435/69.1; 435/320.1; 536/23.1; 536/24.3; 536/24.32; 935/11; 935/21; 935/4; 530/350; 530/324

(58) Field of Search .............................. 435/69.1, 172.3, 435/172.1, 7.1, 6; 530/350, 324; 536/23.1, 24.3, 24.32

(56) References Cited

U.S. PATENT DOCUMENTS

| | | | |
|---|---|---|---|
| 5,444,149 A | 8/1995 | Keene et al. | 530/300 |
| 5,525,495 A | 6/1996 | Keene et al. | 435/172.3 |
| 5,541,291 A | 7/1996 | Keene | 530/350 |
| 5,561,222 A | 10/1996 | Keene et al. | 530/350 |
| 5,773,246 A | 6/1998 | Keene et al. | 435/69.1 |
| 5,866,680 A | 2/1999 | Keene et al. | 530/324 |
| 5,882,866 A | 3/1999 | Keene | 435/6 |
| 5,972,620 A | 10/1999 | Keene | 435/6 |

FOREIGN PATENT DOCUMENTS

| | | | |
|---|---|---|---|
| WO | WO 94/06934 | 3/1994 | C12Q/1/68 |

OTHER PUBLICATIONS

Ceman et al., "Isolation of an FMRP–Associated Messenger Ribonucleoprotein Particle and Identification of Nucleolin and the Fragile X–Related Proteins as Components of the Complex," *Molecular and Cellular Biology*, 19(12):7925–7932 (1999).

International Search Report for PCT/US00/35583, Apr. 18, 2001.

D.E. Tsai et al. In vitro selection of an RNA epitope immunologically cross–reactive with a peptide, *Proc. Natl. Acad. Sci. USA*. 89, 8864–8868 (1992).

S.A. Tenenbaum et al. Identifying mRNA subsets in messenger ribonucleoprotein complexes by using cDNA arrays, *Proc. Natl. Acad. Sci. US* 97 14085–14090 (2000).

J. Keene. Methods and compositions useful in the diagnosis and treatment of autoimmune diseases, *Biotechnology Advances, GB* 15 525 abstract (1997).

J.C. Chambers et al. Isolation and analysis of CDNA clones expressing human lupus La antigen, *Proc. Natl. Acad. Sci.* 82, 2115–2119 (1985).

S.K. Loftus et al. Informatic selection of a neural crest–melanocyte cDNA set for microarray analysis, *Proc. Natl. Acad. Sci. USA* 96, 9277–9280. (1999).

C. M. Perou et al. Distinctive gene expression patterns in human mammary epithelial cells and breast cancers, *Proc. Natl. Acad. of Sci. USA* 96, 9212–9217. (1999).

J.D. Keene, RNA surfaces as functional mimetics of proteins, *Chemistry & Biology* 3, 505–513.

P. Crino et al. Presence and phosphorylation of transcription factors in developing dendrites, *Proc. Natl. Acad. Sci. USA* 95, 2313–2318 (1998).

Q. Zong et al. Messenger RNA translation state: The second dimension of high–throughput expression screening, *Proc. Natl. Acad. Sci. USA* 96, 10632–10636 (1999).

D. Antic et al. Embryonic Lethal Abnormal Visual RNA–binding proteins involved in growth, differentiation, and posttranscriptional gene expression. *American Journal of Human Genetics* 61, 273–278 (1997).

F. Gao et al. Selection of a subset of mRNAs from 3'UTR combinatorial libraries using neuronal RNA–binding protein, Hel–N1. *Proc. Natl. Acad. Sci. USA* 91, 11207–11211 (1994).

(List continued on next page.)

*Primary Examiner*—David Guzo
*Assistant Examiner*—Maria Marvich
(74) *Attorney, Agent, or Firm*—Testa, Hurwitz & Thibeault, LLP

(57) ABSTRACT

Cellular mRNA-protein (mRNP) complexes are partitioned in vivo by contacting a biological sample with at least one ligand that specifically binds at least one component of a mRNP complex. Suitable biological samples comprise at least one mRNA-protein (mRNP) complex and include cell cultures, cell extracts, and whole tissue, including tumor tissue. Ligands include antibodies that specifically bind RNA-binding or RNA-associated proteins present in the mRNP complex. The mRNP complex is separated by binding the ligand with a binding molecule specific for the ligand, where the binding molecule is attached to a solid support. The mRNP complex is collected by removing the mRNP complex from the solid support. After collecting the mRNP complex, the mRNA bound within the complex may be characterized and identified. Subsets of the total mRNA population of a cell may accordingly be characterized, and a gene expression profile of the cell obtained.

49 Claims, 9 Drawing Sheets

OTHER PUBLICATIONS

Buckanovich et al. The Neuronal RNA Binding Protein Nova–1 Recognizes Specific RNA Targets In Vltro and In Vivo. Molecular and Cellular Biology. Jun. 1997. vol 17(6) p 3194–3201.*

Reim et al. The RRM Protein NonA from Drosophila Forms a Complex with the RRM Proteins Hrb87F and S5 and the Zn Finger Protein PEP on hnRNA. Experimental Cell Research. 1999. vol 253 p. 573–586.*

Chu et al. Identification of a Thymidylate Synthase Ribonucleoprotein Complex in Human Cancer Cells. Molecular and Cellular Biology. Jan. 1994, vol 14(1) p 207–213.*

Anderson, N.E., Cunningham, J.M. and Posner, J.B. (1987) Autoimmune pathogenesis of paraneoplastic neurological syndromes. CRC Critical Reviews in Neurobiology. vol. 3, pp. 245–299.

Antic, D., Lu, N. and Keene, J.D. (1999) ELAV tumor antigen, Hel–N1, by increases translation of neurofilament M mRNA and induces formation of neurites in human teratocarcinoma cells. Genes & Development 13,449–461.

Atasoy, U., Watson, J. and Keene, J.D. (1998) ELAV protein HuA (HuR) can redistribute between the nucleus and cytoplasm and is upregulated during serum stimulation and T cell activation. Journal of Cell Science 111, 3145–3156.

Dalmau, J., Furneaux, H., Cordon–Cardo, C. and Posner, J. (1992) The expression of the Hu antigen in human normal and tumor tissues. American Journal of Pathology 141, 881–886.

Duggan, D.J., Bittner, M., Chen, Y., Meltzer, P., Trent, J.M. (1999) Expression profiling using cDNA microarrays. Nature Genetics 21, 10–14.

Fan, X. C. & Steitz, J. A. (1998) Overexpression of HuR, a nuclear–cytoplasmic shuttling protein, increases the in vivo stability of ARE–containing mRNAs. The EMBO Journal 17, 3448–60.

Gao, F.B. and Keene, J.D. (1996) Hel–N1/Hel–N2 proteins are bound to polyA+ mRNA in granular RNP structures and are implicated in neuronal differentiation, Journal of Cell Science 109, 579–589.

Good, P.J. (1995) A conserved family of elav–like genes in vertebrates. Proceedings of the National Academy of Sciences 92, 4557–4561.

Jain, R.G., Andrews, L.G., McGowan, K.M, Pekala, P. and Keene, J.D. (1997) Ectopic expression of Hel–N1, an RNA–binding protein, increases glucose transporter (GLUT1) expression in 3T3–L1 adipocytes. Molecular and Cellular Biology 17, 954–962.

Keene, J.D. (1996) Combinatorial Chemistry: Randomization and Selection of RNA to Identify Targets for RRM RNA–Binding Proteins and Antibodies. In: Methods In Enzymology, J.E. Dahlberg and J.N. Abelson, eds., Academic Press, Inc. San Diego. vol. 267: 367–383.

Keene, J.D. (1999) Invited Commentary: Why is Hu Where? Shuttling of Early–Response Gene Messenger RNA Subsets. Proceedings of the National Academy of Sciences (USA) 96, 5–7.

King, P.H., Levine, T.D., Fremeau, R.T. and Keene, J.D. (1993) Mammalian homologs of Drosophila ELAV localized to a neuronal subset can bind in vitro to the 3' UTR of mRNA encoding the Id transcriptional repressor. Journal of Neuroscience 14, 1943–1952.

Levine, T. D., Gao, F.B., King, P.H., Andrews, L.G. and Keene, J.D. (1994) Hel–N1: an autoimmune RNA–binding protein with specificity for 3' uridylate–rich untranslated regions of growth factor mRNAs. Molecular and Cellular Biology 13, 3494–3504.

Levy, N. S., Chung, S., Furneaux, H. & Levy, A. P. (1998) Hypoxic stabilization of vascular endothelial growth factor mRNA by the RNA–binding protein, HuR. Journal of Biological Chemistry 273, 6417–23.

Lutz–Freyermuth, C. and Keene, J.D. (1989) The U1 RNA binding site of the U1 snRNP–associated A protein suggests a similarity with U2 snRNPs. Molecular and Cellular Biology 9, 2975–2982.

Peng, S., Chen, C. Y., Xu, N. & Shyu, A. B. (1998) RNA stabilization by the AU–rich element binding protein, HuR, and ELAV protein. The EMBO Journal J 17, 3461–70.

Richter, J.D. (1997) Analysis of mRNA Formation and Function. Academic Press, San Diego, pp. 237–261.

Schiavi, S.C., Belasco, J.G. and Greenberg, M.E. (1992) Regulation of proto–oncogene mRNA stability. Biochemical and Biophysical Acta 1114, 95–106.

Sgroi, D.C., Teng, S., Robinson, G., LeVangie, R., Hudson, J.R., Elkahloun, A.G. (1999) In vivo gene expression profile analysis of human breast cancer progression. Cancer Research 59, 5656–5661.

Shimkets et al., Lowe, C.D., Tai, J.T., Sehl, P., Jin, H., Yang, R. et al. (1999) Nature Biotechnology 17, 798–803.

Tsai, D.E., Harper, D.S. and Keene, J.D. (1991) U1snRNP–A protein selects a ten nucleotide consensus sequence from a degenerate RNA pool presented in various structural contexts. Nucleic Acids Research 19, 4931–4936.

Velculescu, V.E., Zhang, L., Vogelstein, B. and Kinzler, K.W. (1995) Serial analysis of gene expression. Science 270, 484–487.

Velculescu, V.E., Zhang, L., Zhou, W., Vogelstein, J., Basrai, M.A., Bassett, D.E., Hieter, P., Vogelstein, B. and Kinzler, K.W. (1997) Cell 88, 243–251.

Wang. W., Caldwell, M.C., Lin, S., Furneaux, H. and Gorospe, M. (2000) HuR regulates cyclin A and cyclin B1 mRNA stability during cell proliferation. The EMBO Journal 19, 1–12.

Wen, X., Fuhrman, S., Michaels, G.S., Carr, D.B., Smith, S., Barker, J.L. and Somogyi, R. (1998) Large–scale temporal gene expression mapping of central nervous system development. Proceedings of the National Academy of Sciences (USA) 95, 334–339.

Yang, G.P., Ross, D.T., Kuang, W.W., Brown, P.O. and Weigel, R.J. (1999) Combining SSH and cDNA microarrays for rapid identification of differentially expressed genes. Nucleic Acids Research 27, 1517–1523.

Zhang, J.–Y., Chan, E.K.L., Peng, X.–X. and Tan, E.M. (1999) A novel cytoplasmic protein with RNA–binding motifs is an autoantigen in human hepatocellular carcinoma. Journal of Experimental Medicine 189, 1101–1110.

Zhao, R., Gish, K., Murphy, M., Yin, Y., Natterman, D., Hoffman, W.H., Tom, E., Mack, D.H. and Levine, A.J. (2000) Analysis of p53–regulated gene expression patterns using oligonucleotide arrays. Genes & Development 14, 981–993.

* cited by examiner

Pre-bleed
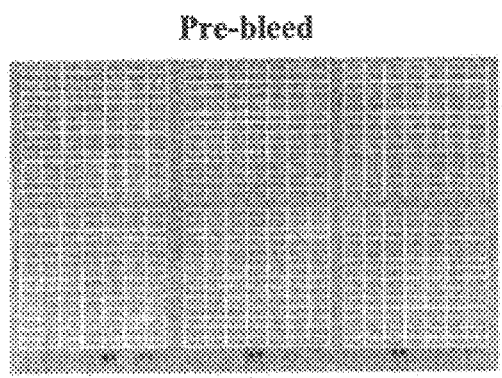
FIG. 5A
PABP mRNP
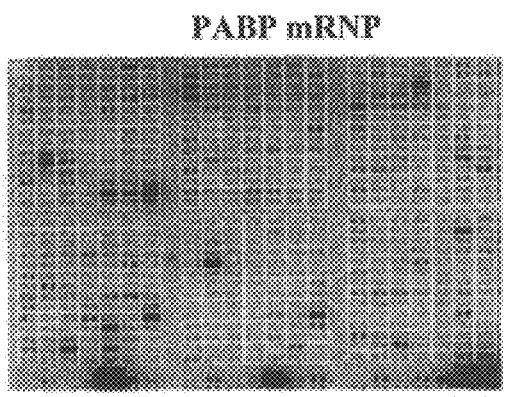

a b
HuB mRNP
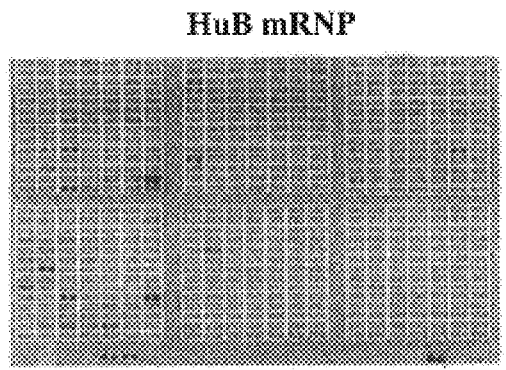

a b
Total RNA
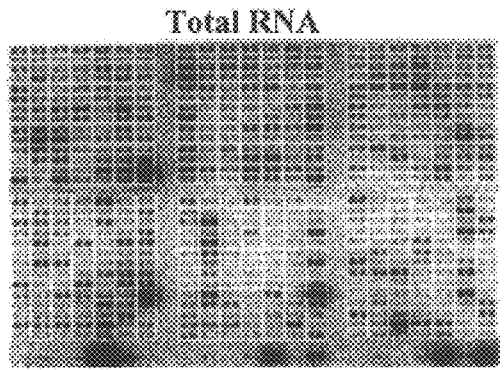

a b
eIF-4E mRNP
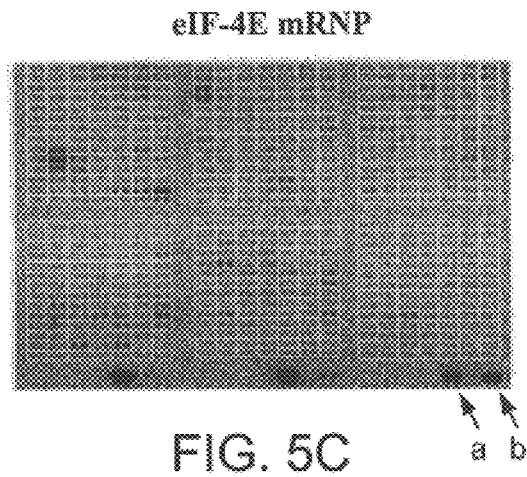

a b

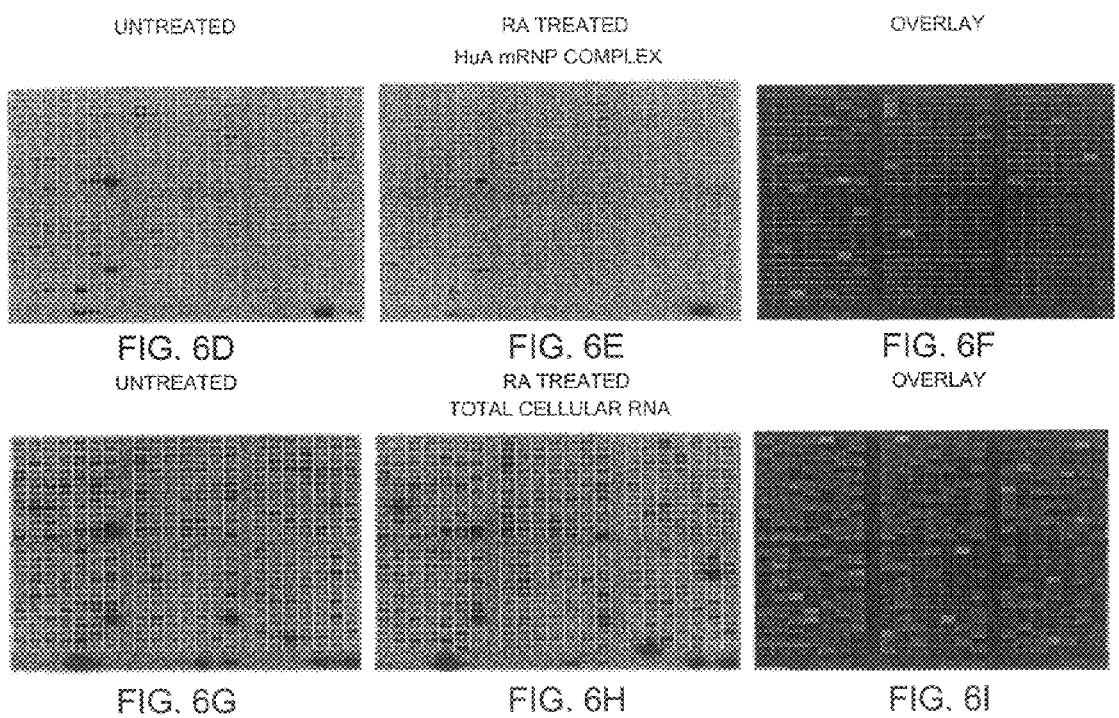

|  | Total | | +RA/−RA | Pellet | | +RA/−RA |
| --- | --- | --- | --- | --- | --- | --- |
|  | −RA | +RA |  | −RA | +RA |  |
| IGF-2 | | | * | | | * |
| INTEGRIN B | | | 1.7 | | | 7.7 |
| CYCLIN D2 | | | 0.7 | | | 4.1 |
| HSP 84 | | | 1.6 | | | 0.2 |

FIG. 7

METHODS FOR ISOLATING AND CHARACTERIZING ENDOGENOUS MRNA-PROTEIN (MRNP) COMPLEXES

RELATED APPLICATIONS

This application claims the benefit of U.S. Provisional Application No. 60/173,338, filed Dec. 28, 1999, which is hereby incorporated in its entirety.

STATEMENT OF FEDERAL SUPPORT

This invention was made with government support under grant number RO1 CA79907 from the National Institutes of Health. The United States government has certain rights to this invention.

FIELD OF THE INVENTION

This invention relates generally to post-transcriptional regulation and methods of profiling gene expression.

BACKGROUND OF THE INVENTION

Many diseases are genetically based, and the genetic background of each individual can have a profound effect on his or her susceptibility to disease. The relatively new field of functional genomics has provided researchers with the ability to determine the functions of proteins based upon knowledge of the genes that encode the proteins. A major goal of functional genomics is to identify gene products that are suitable targets for drug discovery. Such knowledge can lead to a basis for target validation if it is demonstrated that the target of interest has an essential function in a disease. Accordingly, a need exists to develop methods that allow profiling of the gene expression state of cells and tissues in order to understand the consequences of genetics on growth and development.

Understanding global gene expression at the level of the whole cell requires detailed knowledge of the contributions of transcription, pre-mRNA processing, mRNA turnover and translation. Although the sum total of these regulatory processes in each cell accounts for its unique expression profile, few methods are available to independently assess each process en masse.

The expression state of genes in a complex tissue or tumor is generally determined by extracting messenger RNAs from samples (e.g., whole tissues) and analyzing the expressed genes using cDNA libraries, microarrays or serial analysis of gene expression (SAGE) methodologies. See, e.g., Duggan, et al., (1999) *Nature Genetics* 21, 10–14.; Gerhold, et al., (1999) *Trends in Biochemical Sciences* 24, 168–173; Brown, et al., (1999) *Nature Genetics* 21, 38–41; Velculescu, et al., (1995) *Science* 270, 484–487 Velculescu, et al. (1997) *Cell* 88, 243–251. In order to determine the gene expression profile of any single cell type within a tissue or tumor or to recover those messenger RNAs, the tissue must first be subjected to microdissection. This is very laborious, as only a small amount of cellular material is recovered and the purity as well as the quality of the cellular material is compromised.

Post-transcriptional events influence the outcome of protein expression as significantly as transcriptional events. The regulation of transcription and post-transcription are generally linked. Altering the expression of transcriptional activators or repressors has important consequences for the development of a cell. Therefore, feedback loops following translational activation of specific mRNAs may change the program of transcription in response to growth or differentiation signals. DNA arrays are well-suited for profiling the steady-state levels of mRNA globally (i.e., total mRNA or the "transcriptome"). However, because of post-transcriptional events affecting mRNA stability and translation, the expression levels of many cellular proteins do not directly correlate with steady-state levels of mRNAs (Gygi et al. (1999) *Mol. Cell Biol.* 19, 1720–1730; Futcher et al. (1999) *Mol. Cell Biol.* 19, 7357–7368).

Many mRNAs contain sequences that regulate their post-transcriptional expression and localization (Richter (1996) in *Translational Control*, eds. J. W. B Hershey, et al., Cold Spring Harbor Laboratory Press, Cold Spring Harbor, pp. 481–504). These regulatory elements reside in both introns and exons of pre-mRNAs, as well as in both coding and noncoding regions of mature transcripts (Jacobson and Peltz (1996) *Annu. Rev. Biochem.* 65, 693–739; Wickens et al. (1997) *Curr. Opin. Genet. Dev.* 7, 220–232). One example of a sequence-specific regulatory motif is the AU-rich instability element (ARE) present in the 3'-untranslated regions (UTRs) of early-response gene (ERG) mRNAs, many of which encode proteins essential for growth and differentiation (Caput et al. (1986) *Proc. Natl. Acad. Sci. USA* 83, 1670–1674; Shaw and Kamen (1986) *Cell* 46, 659–667; Schiavi et al. (1992) *Biochim. Biophys. Acta* 1114, 95–106; Chen and Shyu (1995) *Trends Biochem. Sci.* 20, 465–470). Regulation via the ARE is poorly understood, but the mammalian ELAV/Hu proteins have been shown to bind to ARE sequence elements in vitro and to affect post-transcriptional mRNA stability and translation in vivo (Jain et al. (1997) *Mol. Cell Biol.* 17, 954–962; Levy et al. (1998) *J. Biol. Chem.* 273, 6417–6423; Fan and Steitz (1998) *EMBO J.* 17, 3448–3460; Peng et al. (1998) *EMBO J.* 17, 3461–3470; Keene (1999) *Proc. Natl. Acad. Sci. USA* 96, 5–7).

In vitro RNA selection methods based upon cellular sequences are reported in Gao et al., *Proc. Natl. Acad. Sci USA* 90, 11207–11211 (1994) and U.S. Pat. Nos. 5,773,246, 5,525,495 and 5,444,149, all to Keene et al., the disclosures of which are incorporated herein in their entirety. Generally, these methods were intended to identify large numbers of mRNAs present in messenger RNP (mRNP) complexes, and utilized in vitro binding and amplification of mRNA sequences from large pools of naturally-occurring mRNAs. These studies used proteins (referred to as ELAV or Hu proteins) known to bind to AU-rich sequence elements present in the untranslated regions of cellular mRNAs. These experiments led to the discovery that mRNAs which are structurally or functionally related may be revealed using multi-targeted RNA binding proteins (i.e., RNA binding proteins that specifically bind more than one target). See Levine, et al., (1994) et al., *Molecular and Cellular Biology* 13, 3494–3504; and King, et al., (1993) *Journal of Neuroscience* 14, 1943–1952; reviewed in Antic and Keene (1997) *American Journal of Human Genetics* 61, 273–278 and Keene (1999) *Proceedings of the National Academy of Sciences (USA)* 96, 5–7. However, these reports are limited to in vitro applications, and do not describe in vivo methods for partitioning RNA into structural or functional subsets using RNA binding proteins. Although in vitro methods have been used to determine protein-RNA interactions, their use has certain limitations. Biochemical methods are generally reliable when carefully controlled, but RNA-binding can be problematic because many interactions may be of low affinity, low specificity or even artifactual. In order to understand RNA-protein interactions and their functional implications on a global systems level it is necessary to find reliable methods to monitor messenger RNP complexes in vivo.

The successful immunoprecipitation of epitope-tagged ELAV/Hu protein which has been transfected into pre-neuronal cells has been reported. See Antic et al., *Genes and Development* 13, 449–461 (1999). This immunoprecipitation was followed by nucleic acid amplification that allowed for the identification of a messenger RNA encoding neurofilament M protein (NF-M).

SUMMARY OF THE INVENTION

The present invention relates to a new, in vivo approach for the determination of gene expression that utilizes the flow of genetic information through messenger RNA clusters or subsets. Recently, the practice of examining multiple macromolecular events simultaneously and in parallel with the goal of organizing such information computationally has taken the designation "-ome." Thus, the genome identifies all of the genes of a cell, while the transcriptome is defined as the messenger RNA complement of the genome and the proteome is defined as the protein complement of the genome (see FIG. 1). The present inventors have defined several physically organized subsets of the transcriptome and defined them as dynamic units of the "ribonome". As described herein, the ribonome consists of a plurality of distinct subsets of messenger RNAs (mRNAs) that are clustered in the cell due to their association with RNA-binding proteins (e.g., regulatory RNA-binding proteins). By identifying the mRNA components of a cellular ribonome, the cellular transcriptome can be broken down into a series of subprofiles that together can be used to define the gene expression state of a cell or tissue (see FIG. 2). In combination with, for example, high throughput approaches and by multiplexing RNA processing assays, the present inventive methods provide the ability to determine the changes that occur in multiple gene transcripts simultaneously.

Accordingly, one aspect of the invention is an in vivo method of partitioning endogenous, cellular mRNA-binding protein (mRNP) complexes. The method, in one embodiment, comprises contacting a biological sample that comprises at least one mRNP complex with a ligand that specifically binds a component of the mRNP complex. The biological sample may be, for example, a tissue sample, whole tissue, a whole organ, a cell culture, or a cell extract or lysate. The component of the mRNP complex may be a RNA binding protein, a RNA-associated protein, a nucleic acid associated with the mRNP complex including the mRNA itself, or another molecule or compound (e.g., carbohydrate, lipid, vitamin, etc.) that associates with the mRNP complex. The ligand may be, for example, an antibody that specifically binds the component, a nucleic acid that binds the component (e.g., an antisense molecule, a RNA molecule that binds the component), or any other compound or molecule that binds the component of the complex. The mRNP complex is then separated by binding the ligand (now bound to the mRNP complex) to a binding molecule that binds the ligand. The binding molecule may bind the ligand directly (i.e., may be an antibody specific for the ligand), or may bind the ligand indirectly (i.e., may be an antibody or binding partner for a tag on the ligand). The binding molecule will be attached to a solid support, such as a bead or plate or column, as known in the art. Accordingly, the mRNP complex will be attached to the solid support via the ligand and binding molecule. The mRNP complex is then collected by removing it from the solid support (i.e., the complex is washed off the solid support using suitable conditions and solvents).

The identity of the mRNA bound within the mRNP complex may then be determined, for example, by separating the mRNA from the complex, reverse transcribing the mRNA into cDNA, and sequencing the cDNA.

In embodiments of the invention, therefore, the mRNP complex may be isolated by direct immunoprecipitation of the mRNP complexes, either with or without epitope tags, or by other biochemical partitioning methods. For example, other proteins bound to or associated with the mRNP complex may be immunoprecipitated in order to recover the mRNP complex and subsequently the mRNAs bound within the complex. The skilled artisan will appreciate that embodiments of the inventive method allow for the identification of a plurality of mRNA complexes simultaneously (i.e., concurrently), sequentially, or in batch-wise fashion. Alternatively, the method may be carried out on one biological sample (or portion thereof) numerous times, the steps of the method being performed in a sequential fashion, with each iteration of the method utilizing a different ligand. In any of the described embodiments, cDNA or genomic microarray grids, for example, may be used to identify mRNAs isolated by the inventive method en masse.

A "subset" of mRNA is defined as a plurality of mRNA transcripts or messages that specifically bind or associate with a mRNP complex. In other words, subsets are defined by their ability to bind within or to a particular mRNP complex. The subset will preferably be a quantitative or qualitative fraction of the total mRNA population of the cell. Furthermore, subsets within subsets of mRNAs may be identified using the invention. The collection of mRNA subsets for any particular cell or tissue sample is an expression profile, also referred to herein as a "ribonomic profile," for that cell or tissue. It will be appreciated that expression profiles will differ from cell sample to cell sample, depending on the type of cell in the sample (e.g., what species or tissue type the cell is), the differentiation status of the cell, the pathogenicity of the cell (i.e., if the cell is infected or if it is expressing a deleterious gene, such as an oncogene, or if the cell is lacking a particular gene), the specific ligand used to isolate the mRNP complex, etc. Thus, the expression profile of a cell may be used as an identifier for the cell, enabling the artisan to compare and distinguish profiles of different cells.

Stated otherwise, the ribonomic profile provides a pattern recognition subset of the global mRNA profile of the cell. When the growth state of the cells changes (i.e., tumorigenesis) or the cell is perturbed by a pathogen (i.e., a viral infection), the profile will change, and a perturbation of the ribonome can be detected. If cells are treated with compounds (i.e., drugs) the ribonomic patterns will show desirable or undesirable alteration. Accordingly, the new method provides methods for evaluating the effect of numerous factors on a cell, including toxicity, aging, apoptosis, pathogenesis and cell differentiation.

The new invention has several advantages over previous methods of partitioning RNA. First, partitioning of mRNP complexes may be carried out in vivo, while previous methods were limited to in vitro applications. The new method is robust enough such that amplification (e.g., by PCR, or alternatively according to the method of Antic et al. (1999) *Genes Dev.* 13, 449–461) is not necessary to identify cDNAs of interest once they are reverse transcribed from the isolated subset of mRNAs. The present invention does not require the use of iterative processes, such as those set forth in Gao et al. supra. Finally, quantitative determinations are possible with the present invention if, for example, hybridization is used to analyze the expression profile of the cell (e.g., in microarray assays or RNAse protection assays (RPA)).

In certain embodiments, therefore, the present invention advantageously allows the artisan to identify, monitor, and quantitate mature gene transcripts en masse in order to determine their localization, activity, stability, and translation into protein components of living cells. The methods described herein advantageously provide a novel approach to functional genomics by providing methods of isolating endogenous messenger-RNA binding proteins, and methods of identifying the subset of cellular mRNAs contained in mRNP-complexes, using microarrays or other known procedures. In preferred embodiments, the inventive method provides a basis for investigating and determining functional mRNA networks during growth and differentiation cycles by using mRNA-binding proteins and other mRNP-associated factors to define mRNA subsets.

It will be appreciated that patterns of mRNA subsets (i.e., expression profiles) may be altered in the presence of certain compounds (i.e., drugs) or under various disease conditions. Accordingly, in certain embodiments the inventive methods are useful for screening compounds that may be of therapeutic use, and for finding appropriate gene targets for the compounds. In other embodiments, the inventive method is useful for determining the disease state of a cell, thus providing means for classifying or diagnosing the presence or predisposition for disease (e.g., cancer).

Gene expression profiles will also vary between differing cell types present in a complex tissue, such as a tumor. Some mRNA binding proteins are present only in certain tumor cells, and a tumor may comprise more than one cell type. Gene expression profiling for each cell type within a tumor or tissue may be carried out by making an extract of the tissue and immunoprecipitating cell-type specific components of mRNP complexes (e.g., RNA-binding proteins that are attached to mRNA) directly from the extract (i.e., in vivo). The immunoprecipitated pellets will contain mRNAs that are only present in the same cells that contain the attached or associated component. Thus, in certain embodiments, the inventive methods may be used to characterize and distinguish the gene expression profiles of a plurality of cell types, which cell types may co-exist in the same complex tissue. This can allow the tumor cells to be profiled in whole tumor extracts without having to analyze mRNA in, for example, the non-tumor stromal cells and blood cells that surround tumor cells. The results of such characterization may be useful in determining, for example, the proper course of treatment for a patient suffering with a tumor, when the choice of treatment depends of the kind of tissue (e.g., endothelial vascular tissue) present in a tumor.

In another embodiment, the present invention provides methods for isolating and optionally identifying proteins that bind or associate with a mRNP complex.

Alternatively, and in another embodiment, the inventive method may be used to screen test compounds for their ability to modulate gene expression in a cell. Such methods are useful for screening putative drugs that may be used in the treatment and/or prevention of disorders associated with irregularities in gene expression, including but not limited to cancer.

The foregoing and other aspects of the present invention are explained in detail in the specification set forth below.

BRIEF DESCRIPTION OF THE DRAWINGS

FIG. 3A and 3B show examples of mMyc and mCyc-1 multi-probe template sets, respectively. Lanes: (1) undigested riboprobe (slightly larger than RNase-digested product due to riboprobe plasmid template); (2) total cellular RNA; (3) rabbit pre-bleed serum control; (4) mRNAs extracted from HuB mRNPs; (5) mRNAs extracted from PABP mRNPs. An asterisk (*) denotes mRNA species not detected in total RNA.

For panels C, F, and I: green bars indicate mRNAs of approximately equal abundance; red bars represent mRNAs from HuB mRNPs that were detectable at four-fold or greater following RA treatment; blue bars represent mRNAs from HuB mRNPs that were detectable four-fold or greater in cells before RA treatment.

FIG. 7 is a schematic of ribonomic profiling.

Figure 8:
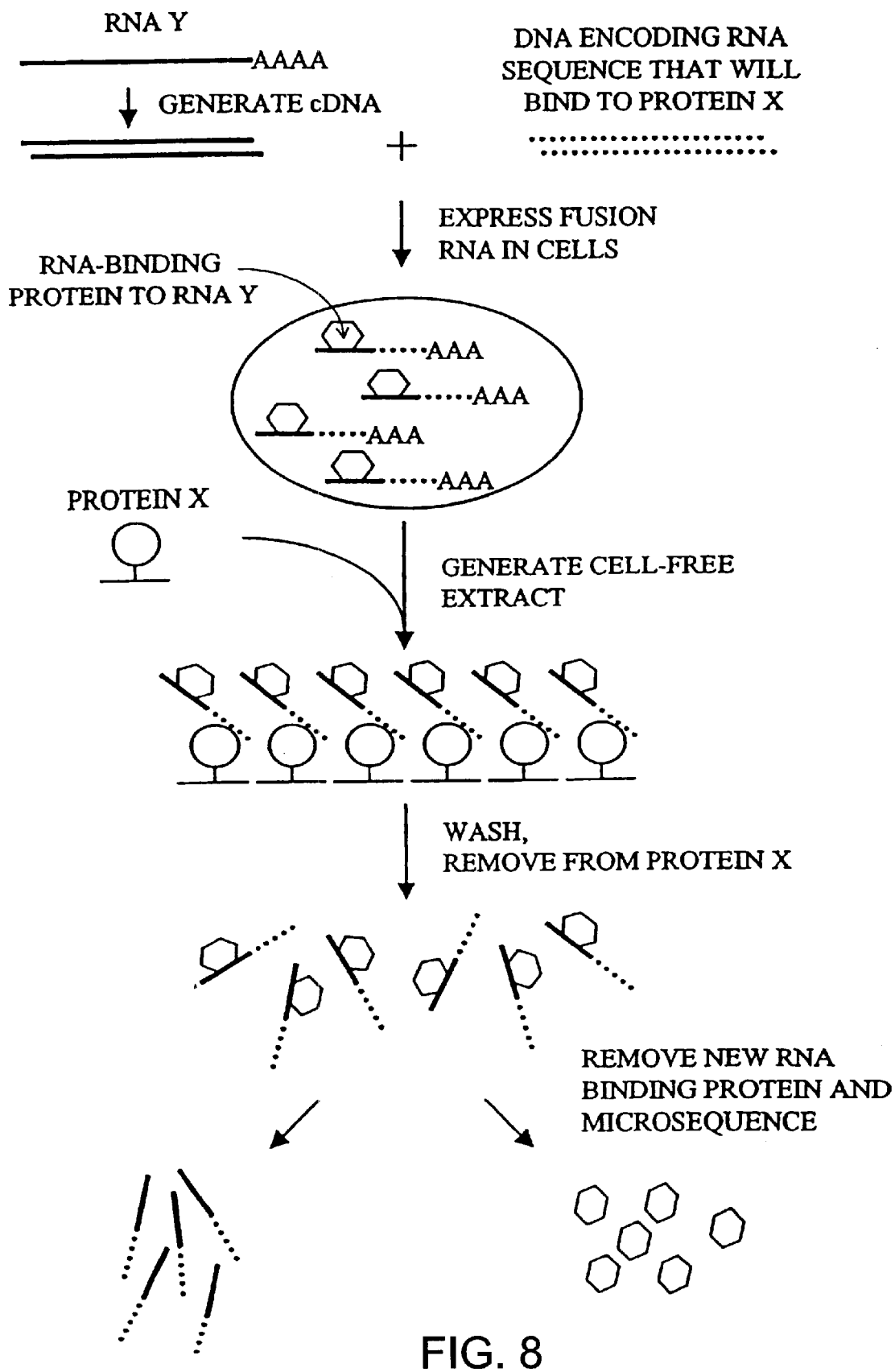

FIG. 8 is a schematic outlining a strategy for the identification of new RNA-binding proteins.

DETAILED DESCRIPTION OF PREFERRED EMBODIMENTS

The present invention will now be described more fully with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only, and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Except as otherwise indicated, standard methods may be used for the production of cloned genes, expression cassettes, vectors, and transformed cells and plants according to the present invention. Such methods are known to those skilled in the art. See e.g., J. Sambrook et al., *Molecular Cloning: A Laboratory Manual Second Edition* (Cold Spring Harbor Laboratory, Cold Spring Harbor, N.Y., 1989); F. M. Ausubel et al., *Current Protocols In Molecular Biology* (Green Publishing Associates, Inc. and Wiley-Interscience, New York, 1991).

Nucleotides and amino acids are represented herein in the manner recommended by the IUPAC-IUB Biochemical Nomenclature Commission, or (for amino acids) by three letter code, in accordance with 37 C.F.R. §1.822 and established usage. See, e.g., *Patentin User Manual*, 99–102 (November 1990) (U.S. Patent and Trademark Office).

Nucleotide sequences are presented herein by single strand only, in the 5' to 3' direction, from left to right. "Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences, and as well as the sequence explicitly indicated. Two nucleic acids are "recombined" when sequences from each of the two or more nucleic acids are combined in a progeny nucleic acid.

The terms "nucleic acid" or "nucleic acid sequence" may also be used in reference to genes, cDNA, and mRNA encoded by a gene. The term "gene" is used broadly to refer to any segment of DNA associated with a biological function. Thus, genes include coding sequences and/or the regulatory sequences required for their expression. Genes also include non-expressed DNA segments that, for example, form recognition sequences for other proteins. Genes can be obtained from a variety of sources, including cloning from a source of interest or synthesizing from known or predicted sequence information.

As used herein, a nucleic acid molecule may be RNA (the term "RNA" encompassing all ribonucleic acids, including but not limited to pre-mRNA, mRNA, rRNA, hnRNA, snRNA and tRNA); DNA; peptide nucleic acid (PNA, as described in, e.g., U.S. Pat. No. 5,539,082 to Nielsen et al., and U.S. Pat. No. 5,821,060 to Arlinghaus et al.); and the analogs and modified forms thereof. Preferably, the nucleic acid is RNA, and more preferably the nucleic acid molecule is messenger RNA (mRNA). Nucleic acid molecules of the present invention may be linear or circular, an entire gene or a fragment thereof, full-length or fragmented/digested, "chimeric" in the sense of comprising more than one kind of nucleic acid, and may be single-stranded or double-stranded. Nucleic acid from any source may be used in the present invention; that is, nucleic acids of the present invention include but are not limited to genomic nucleic acid, synthetic nucleic acid, nucleic acid obtained from a plasmid, cDNA, recombinant nucleic acid, and nucleic acid that has been modified by known chemical methods, as further described herein. Nucleic acids may also be products of in vitro selection experiments (also called aptamers) and other nucleic acid molecules useful for their ability to bind or be bound by other ligands. See D. Kenan, *TIBS* 19, 57–64 (1994); L. Gold, et al., *Annu. Rev. Biochem.* 64, 763–798 (1995); S. E. Osborne and A. D. Ellington, *Chem. Rev.* 97, 349–370 (1997).

Nucleic acids of the present invention may be obtained from any organism, including but not limited to bacteria, viruses, fungi, plants and animals, with animal nucleic acid being preferred, mammalian nucleic acid being more preferred, and human nucleic acid being most preferred. If desired, the nucleic acid may be amplified according to any of the known nucleic acid amplification methods that are well-known in the art (e.g., PCR, RT-PCR, QC-PCR, SDA, and the like). Nucleic acids of the present invention may be, and preferably are, purified according to methods known in the art.

As summarized above, the present invention relates to in vivo methods for partitioning mRNP complexes from a cell. mRNP complexes of the present invention is preferably from a biological sample, such as a tissue sample, whole tissue, a whole organ (e.g., an entire brain, liver, kidney, etc.), bodily fluid sample, cell culture, cell lysate, cell extract or the like. In a preferred embodiment, the biological sample comprises or is obtained from a population of cells. By a "population of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures, or from a complex tissue such as a tumor, or may alternatively contain only a single cell type. In a preferred embodiment, cells that are proliferating are used. Alternatively, non-proliferating cells may be used.

Preferred cell types for use in the invention include, but are not limited to, mammalian cells, including animal (rodents, equines, bovines, canines, felines and primates), and human cells, with human cells being preferred. Cells from non-mammalian animals (e.g., avians, fish, reptiles) and from plants may also be used in the practice of the present invention. Cells may be tumor cells from tumors of any type, including breast, skin, lung, cervix, colorectal, and brain/CNS tumors, etc. Additionally, non-cancerous cells from any organ may be used, including liver cells, neurons, muscle cells, and the like.

mRNA is referred to herein interchangeably as a "message" or a "transcript". A "subset" of mRNA is defined as a plurality of mRNA that specifically binds within a particular mRNA binding protein complex (mRNP complex). Thus, subsets are defined by their ability to bind within or to a particular mRNP complex. The mRNA subset will preferably be a fraction of the total mRNA population of the cell.

As summarized above, one aspect of the invention is an in vivo method of partitioning endogenous cellular mRNA-binding protein (mRNP) complexes. "Endogenous" is used herein to mean that the mRNP complex forms in a cell (i.e., in vivo or in situ). The mRNP complex may form in the cell naturally, i.e., the components of the mRNP complex naturally occur in the cell and form the mRNP complex. Alternatively, the mRNP complex forms in a cell, even though one or more components of the complex is introduced into the cell by, e.g., infection or transformation. For example, a mRNP complex endogenously forms in a cell when a RNA-binding protein that is a component of the mRNP complex is ectopically expressed in the cell by (for example) transforming the cell or infecting the cell with an expression vector that carries nucleic acid encoding the protein, and a mRNP complex in which the protein binds is formed.

The method, in one embodiment, comprises contacting a biological sample that comprises at least one mRNP complex with a ligand that specifically binds a component of the mRNP complex. The component of the mRNP complex may be a RNA binding protein, a RNA-associated protein, a nucleic acid associated with the mRNP complex including the mRNA itself, or another molecule or compound (e.g., carbohydrate, lipid, vitamin, etc.) that associates with the mRNP complex. A component "associates" with a mRNP complex if it binds or otherwise attaches to the mRNP complex with a Kd of about $10^{-6}$ to about $10^{-9}$. In a preferred embodiment, the component associates with the complex with a Kd of about $10^{-7}$ to about $10^{-9}$. In a more preferred embodiment, the component associates with the complex with a Kd of about $10^{-8}$ to about $10^{-9}$.

The ligand may be any molecule that specifically binds the component of the mRNP complex. For example, the ligand may an antibody that specifically binds the component, a nucleic acid that binds the component (e.g., an antisense molecule, a RNA molecule that binds the component), or any other compound or molecule that specifically binds the component of the complex. In certain embodiments, the ligand may be obtained by using the serum of a subject (i.e., a human or animal subject) that has a disorder known to be associated with the production of mRNP-complex specific antibodies or proteins. Examples of these disorders include autoimmune disorders such as systemic lupus erythematosus ("lupus" or SLE) and a number of cancers. In certain embodiments, the ligand may be "tagged" with another compound or molecule in order to facilitate the separation, observation or detection of the ligand. In one embodiment of the invention, the ligand is "epitope tagged," as described in the art. Suitable tags are known in the art and include but are not limited to biotin, the MS2 protein binding site sequence, the U1snRNA 70 k binding site sequence, the U1snRNA A binding site sequence, the g10 binding site sequence (commercially available from Novagen, Inc., Madison, Wis., USA), and FLAG-TAG® (Sigma Chemical, St. Louis, Mo., USA).

The mRNP complex is then separated by binding the ligand (now bound to the mRNP complex) to a binding molecule that specifically binds the ligand. The binding molecule may bind the ligand directly (i.e., may be an antibody or protein specific for the ligand), or may bind the ligand indirectly (i.e., may be an antibody or binding partner for a tag on the ligand). Suitable binding molecules include but are not limited to protein A, protein G, streptavidin. Binding molecules may also be obtained by using the serum of a subject suffering from, for example, an autoimmune disorder or cancer. In certain embodiments, the ligand is an antibody that binds the component of the mRNP complex via the Fab region of the antibody, and the binding molecule in turn binds the Fc region of the antibody. The binding molecule will be attached to a solid support, such as a bead, well, pin, plate or column, as known in the art. Accordingly, the mRNP complex will be attached to the solid support via the ligand and binding molecule.

The mRNP complex is then collected by removing it from the solid support (i.e., the complex is washed off the solid support under appropriate stringency conditions, using suitable solvents that may be determined by skilled artisans).

In certain embodiments of the invention, the mRNP complex may be stabilized by cross-linking prior to binding the ligand thereto. Cross-linking, as used herein, means covalently binding (e.g., covalently binding the components of the mRNP complex together). Cross-linking may be contrasted with ligand-target binding, or binding molecule-ligand binding, which is generally non-covalent binding. Cross-linking may be carried out by physical means (e.g., by heat or ultraviolet radiation), or chemical means (e.g., by contacting the complex with formaldehyde, paraformaldehyde, or other known cross-linking agents), which means are known or determinable by those skilled in the art. In other embodiments, the ligand may be cross-linked to the mRNP complex after binding the mRNP complex. In additional embodiments, the binding molecule may be cross-linked to the ligand after binding to the ligand. In yet other embodiments, the binding molecule may be cross-linked to the solid support.

The skilled artisan will appreciate the inventive method allows for the identification of a plurality of mRNP complexes simultaneously (e.g., "en masse"). For example, a biological sample may be contacted with a plurality of ligands specific for different mRNP complex components. A plurality of mRNP complexes from the sample will bind the various ligands. The plurality of mRNP complexes can then be separated using appropriate binding molecules, thus isolating the plurality of mRNP complexes. The mRNP complexes and the mRNAs contained within the complexes may then be characterized and/or identified by methods described herein and known in the art. Alternatively, the method may be carried out on one sample numerous times, the inventive steps being performed in a sequential fashion, with each iteration of steps utilizing a different ligand.

As set forth above, a subset of mRNA identifies a pattern-recognition profile that is characteristic of the RNA structural or functional networks in that sample. The collection of mRNA subsets for any particular cell or tissue sample constitutes a gene expression profile, and more specifically a ribonomic gene expression profile, for that cell or tissue. It will be appreciated that ribonomic expression profiles may differ from cell to cell, depending on the type of cell in the sample (e.g., what species or tissue type the cell is), the differentiation status of the cell, the viability of the cell (i.e., if the cell is infected or if it is expressing a deleterious gene, such as an oncogene, or if the cell is lacking a particular gene or not expressing a particular gene), the specific ligands used to isolate the mRNP complexes, etc. Thus, the ribonomic expression profile of a cell may be used as an identifier for the cell, enabling the artisan to compare and distinguish profiles or subprofiles of different cells. The genes identified by the RNAs present in each ribonomic pattern form distinct subsets that may be associated with a particular cell cycle, stage of differentiation, apoptosis or stress induction, viral infection, or cancer.

cDNAs may be used to identify mRNP complexes partitioned with a ligand or ligands specific for a component of the mRNP complex. cDNA microarray grids, for example, may be used to identify mRNA subsets en masse. Microarrays are precisely aligned grids in which each target nucleic acid (e.g., gene) has a position in a matrix of carefully spotted cDNAs. See Gerhold et al. supra, Duggan et al. supra, and Brown et al., supra. Alternatively, genomic microarrays (e.g., microarrays wherein the target nucleic acids may contain introns and exons) may be used. Therefore, each gene or target nucleic acid being examined on a microarray has a precise address that can be located, and the binding can be quantitated. Microarrays in the form of siliconized chips or those based upon cDNA blots on nylon or nitrocellulose are commercially available. Glass slides can also be customized with oligonucleotides or DNAs for detection of complementary RNA sequences. In all of these cases, the hybridization platforms allow identification of the mRNAs in a sample based upon the stringency of binding and washing. This has been referred to as "sequencing by hybridization." Although microarray technology is one method of analysis, it is only one way to identify and/or sequence the mRNAs in the mRNA subset. Alternative approaches include but are not limited to differential display, phage display/analysis, SAGE or simply preparing cDNA libraries from the mRNA preparation and sequencing all members of the library.

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

In a preferred embodiment, amplification of the mRNA isolated according to the present invention, and/or the cDNA obtained from the mRNA is not carried out during the identification of the nucleic acid, and is not necessary or required by the present invention. However, the skilled artisan may choose to amplify the nucleic acid that is the subject of identification (e.g., the nucleic acid being identified via microarray analysis and/or sequencing) for convenience, as a matter of preference, and/or to comply with the specification/instructions of certain commercially available microarrays or microarray analysis systems. Thus, if desired, the nucleic acid may be amplified according to any of the numerous known nucleic acid amplification methods that are well-known in the art (e.g., PCR, RT-PCR, QC-PCR, SDA, and the like).

Methods of the present invention may be carried out in several ways, according to the needs of the practitioner and the purpose for which the invention is carried out. For example, in one embodiment, mRNA-binding protein complexes that are unique to a cell type of interest are identified. In an example of such an embodiment, an antibody that is specific for the mRNP complex can be used to immunoprecipitate the complex with its associated mRNAs. The RNAs may then identified to form the ribonomic expression profile of that cell type, or alternatively may be isolated for (as an example) drug screening. The mRNA candidates for post-transcriptional regulation may be analyzed en masse, as a subset, for changes in mRNA stability during the cell cycle or developmental events. In certain embodiments, the methods may be carried out by isolating nuclei from cells undergoing developmental or cell cycle changes, performing nuclear run-off assays according to known techniques to obtain transcribing mRNAs, and then comparing the transcribing mRNAs with the global mRNA levels in the same cells using cDNA microarrays. These methods thus provide the ability to distinguish transcriptional from post-transcriptional effects on steady state mRNA levels en masse.

In another embodiment, cells in culture are transformed to express a RNA-binding protein (RBP) or RNA-associated protein (RAP) that will associate with particular mRNAs only in a cell type of interest. DNA encoding the RBP or RAP may be carried by a recombinant vector (e.g., a plasmid, a viral vector) and transformed into the cell by known means, after which the RBP or RAP is expressed in the cell. Any RBP or RAP can be used, as described further herein. The protein may be in its native form, or it may be tagged (e.g., epitope tagged) for easy recovery from the cell. Detection of multiple RNA targets in vivo that are bound or associated with RBPs or RAPs may be carried out by using accessible epitopes, if necessary, but preferably is carried out without tags. In cases where the epitopes on the RBPs or RAPs are inaccessible or obscured, epitope tags on ectopically expressed recombinant proteins may be used. The transformed cell may be mixed with other cell types or may be implanted in an animal or human subject. A ligand (e.g., an antibody) that is specific for the protein can used to immunoprecipitate the protein with its associated messenger RNAs from an extract of a tissue containing the transformed cell. The mRNA complexes and its associated RNAs may then identified to form the expression profile of that cell type or is otherwise analyzed (e.g., for drug development).

In still another embodiment, a specific cell type in an animal is engineered with one or more cell-type specific gene promoters to express a RBP or RAP in the cell type of interest. As set forth above, the gene promoter and the RBP or RAP may be carried on one or more vectors and transformed into the cell, where the RBP or RAP is expressed. In one embodiment, a ligand (e.g., an antibody) that is specific for this protein can used to immunoprecipitate the protein with its attached or associated messenger RNAs from an extract of a tissue containing the cell type of interest. The RNAs are then identified to form the expression profile of that cell type or isolated, e.g., for drug development.

RNA binding proteins (RBPs) and RNA-associated proteins (RAPs) useful in the practice of the present invention are known in the art, or may alternatively be identified and discovered by methods described herein. RNA binding proteins are now known to be involved in the control of a variety of cellular regulatory and developmental processes, such as RNA processing and compartmentalization, RNA stabilization, mRNA translation and viral gene expression. RNA binding proteins include poly A-binding protein ("PABP," which gives rise to a subset of the total mRNA population that is quantitatively different from the total mRNA population), and other general RNA binding proteins, as well as RNA-binding proteins that are attached to only one or a few messenger RNAs in a particular cell type. Other useful proteins are autoantibodies reactive with RNA and RNA-binding proteins.

Examples of useful RNA binding proteins include the four ELAV/Hu mammalian homologues of the Drosophila ELAV RNA-binding protein (Good (1995) *Proc. Natl. Acad. Sci. USA* 92, 4557–4561; Antic and Keene, supra. HuA (HuR) is ubiquitously expressed while HuB, HuC and HuD (and their respective alternatively-spliced isoforms) are predominantly found in neuronal tissue, but can also be expressed as tumor cell-specific antigens in some small cell carcinomas, neuroblastomas, and medulloblastomas (reviewed in Keene (1999) *Proc. Natl. Acad. Sci. USA* 96, 5–7). All Hu proteins contain three RNA-recognition motifs (RRMs), which confer their binding specificity for AREs (Antic and Keene, supra; Kenan et al. (1991) *Trends Biochem. Sci.* 16, 214–220; Burd and Dreyfuss (1994) *Science* 265, 615–621). The evidence for ARE binding by Hu proteins began with the identification of an AU-rich binding consensus sequence from a randomized combinatorial RNA library that was screened with recombinant HuB (Levine et al. (1993) *Mol. Cell Biol.* 13, 3494–3504; Gao et al. (1994) *Proc. Natl. Acad. Sci. USA* 91, 11207–11211). These and other studies demonstrated that Hu proteins bind in vitro to several ARE-containing ERG mRNAs including c-myc, c-fos, GM-CSF and GAP-43 (Levine et al. (1993) *Mol. Cell Biol.* 13, 3494–3504; Gao et al. (1994) *Proc. Natl. Acad. Sci. USA* 91, 11207–11211; King et al. (1994) *J. Neurosci.* 14, 1943–1952; Liu et a. (1995) *Neurology* 45, 544–550; Ma et al (1996) *J. Biol. Chem.* 271, 8144–8151; Abe et al. (1996) *Nucleic Acids Res.* 24, 2011–2016; Chung et al. (1997) *J. Biol. Chem.* 272, 6593–6598; Fan and Steitz (1998) *EMBO J.* 17, 3448–3460; Antic et al. (1999) *Genes Dev.* 13, 449–461).

The binding of Hu proteins to ARE-containing mRNAs can result in the stabilization and increased translatability of the mRNA transcripts (Jain et al. (1997) *Mol. Cell Biol.* 17, 954–962; Levy et al. (1998) *J. Biol. Chem.* 273, 6417–6423; Fan and Steitz (1998) *EMBO J.* 17, 3448–3460; Peng et al. (1998) *EMBO J.* 17, 3461–3470). The neuron-specific Hu proteins are one of the earliest neuronal markers produced in teratocarcinoma cells following retinoic acid (RA)-treatment to induce neuronal differentiation (Antic et al., supra; Gao and Keene (1996) *J. Cell Sci.* 109, 579–589).

In one embodiment, the ligand used to carry out the invention is a RNA binding protein selected from the RNA Recognition Motif (RRM) family of cellular proteins involved in pre-messenger RNA processing. One example of such a protein is the U1A snRNP protein. More than 200 members of the RRM superfamily have been reported to date, the majority of which are ubiquitously expressed and conserved in phylogeny (Query et al, *Cell* (1989) 57: 89–101; Kenan et al, *Trends Biochem. Sci.* (1991)16: 214–220). Most are known to have binding specificity for polyadenylate mRNA or small nuclear ribonucleic acids (e.g. U1, U2, etc.) transfer RNAs, 5S or 7S RNAs. They include but are not limited to hnRNP proteins (A, B, C, D, E, F, G, H, I, K, L), RRM proteins CArG, DT-7, PTB, K1, K2, K3, HuD, HUC, rbp9, eIF4B, sxl, tra-2, AUBF, AUF, 32KD protein, ASF/SF2, U2AF, SC35, and other hnRNP proteins. Tissue-specific members of the RRM family are less common, including IMP, Bruno, AZP-RRMI, X16 which is expressed in pre-B cells, Bj6 which is a puff-specific Drosophila protein and ELAV/Hu, which are neuron specific.

RNA-binding and RNA-associated proteins useful in the practice of the present invention include those isolated using autoimmune and cancer patient sera. A non-comprehensive list of RNA-binding and RNA-associated proteins useful in the practice of the present inventions is set forth below in Table 1.

TABLE 1

RNA Binding and RNA Associated Proteins

| | | |
|---|---|---|
| SLBP | DAN | TTP |
| Hel-N1 | Hel-N2 | eIF-4A |
| eIF-4B | eIF-4G | eIF-4E |
| eIF-5 | eIF-4EBP | MNK1 |
| PABP | p62 | KOC |
| p90 | La | Sm |
| Ro | U1-70K | AUF-1 |
| RNAse-L | GAPDH | GRSF |
| Ribosomal Po, P1, P2/L32 | PM-Scl | FMR |
| Stauffen | Crab 95 | TIA-1 |
| Upf1 | RNA BP1 | RNA BP2 |
| RNA BP3 | CstF-50 | NOVA-1 |
| NOVA-2 | CPEBP | GRBP |
| SXL | SC35 | U2AF |
| ASF/SF2 | ETR-1 | IMP-1 |
| IMP-2 | IMP-3 | ZBP |
| LRBP-1 | Barb | PTB |
| uPAmRNA BP | BARB1 | BARB2 |
| GIFASBP | CYP mRNA BP | IRE-BP |
| p50 | RHA | FN mRNA BP |
| AUF-1 | GA mRNA BP | Vigillin |
| ERBP | CRD-BP | HuA |
| HuB | HuC | HuD |
| hnRNP A | hnRNP B | hnRNP C |
| hnRNP D | hnRNP E | hnRNP F |
| hnRNP G | hnRNP H | hnRNP K |
| hnRNP L | U2AF | |

The identification of new (i.e., novel, previously unknown) RNA-binding proteins (RBPs) and RNA associated proteins, is another aspect of the invention. Thus, in one embodiment of the invention, a RNA of interest (depicted in FIG. 8 as "RNA Y") is used as a "bait" to trap a new RBP or RAP. In a preferred embodiment, RNA Y is first converted to a cDNA using standard molecular biology techniques and is subsequently ligated at the 3' or 5' end to another fragment of DNA (referred to herein as the "tagging DNA") that encodes a sequence (e.g., a RNA) that will bind a ligand of the present invention (the ligand being illustrated as protein "X" in FIG. 8). In other words, the tagging DNA encodes a binding partner of the ligand. Useful ligands may, in some embodiments, be obtained from (i.e., by using) the serum of a subject (i.e., a human or animal subject) that has a disorder known to be associated with the production of mRNP-complex specific antibodies or proteins, including autoimmune disorders and cancer. Useful binding partners include antibodies to the ligand.

The resulting DNA chimera is fused to a promoter in an expression vector (e.g., a plasmid) and expressed in living cells (e.g., in a cell culture) to produce a RNA fusion molecule. In an alternative embodiment, the expression vector is infected into the cells by a virus, preferably a recombinant virus. A cell-free extract from the culture is prepared and contacted with the ligand (e.g., protein X) which has been immobilized on a solid support. After an incubation period, the ligand and the attached/associated RNA fusion molecule and its associated RBPs or RAPs are washed to remove residual cellular material. After the wash step, the RBPs or RAPs are removed from the RNA-protein complex and analyzed (e.g., sequenced using standard methods of microsequencing).

Once partial protein sequence is obtained, the corresponding gene may be identified from known databases containing cDNA and genomic sequences. Preferably, the gene is isolated, the protein is expressed, and an antibody is generated against the recombinant protein using known techniques. The antibodies are then used to recover and confirm the identity of the endogenous RBP or RAP. Subsequently, the antibody can be used for ribonomic analysis (see examples below) to determine the subset of cellular RNAs that cluster with (i.e., associate with) RNA Y. Furthermore, the RBP or RAP may be tested for its ability to regulate the translation of the protein encoded by RNA Y, and may be tested for validation as a drug target. Likewise, proteins encoded by the cellular RNAs that cluster with RNA Y may be tested for validation as drug targets, as further described herein.

Antibodies that specifically bind mRNP complexes are thus an aspect of the invention. Antibodies to mRNP complexes may be generated using methods that are well known in the art. Such antibodies may include, but are not limited to, polyclonal, monoclonal, chimeric, single chain, Fab fragments, and fragments produced by a Fab expression library. Antibodies and fragments thereof may also be generated using antibody phage expression display techniques, which are known in the art.

For the production of antibodies, various hosts including goats, rabbits, rats, mice, humans, and others, may be immunized by injection with the mRNP complex or any fragment or component thereof which has immunogenic properties. Depending on the host species, various adjuvants may be used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacilli Calmette-Guerin) and *Corynebacterium parvum* are especially preferable.

Monoclonal antibodies to the components of the mRNP complex may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256:495–497; Kozbor, D. et al. (1985) *J. Immunol. Methods* 81:31–42; Cote, R. J. et al. (1983) *Proc. Natl. Acad. Sci.* 80:2026–2030; Cole, S. P. et al. (1984) *Mol. Cell Biol.* 62.109–120). Briefly, the procedure is as follows: an animal is immunized with the mRNP complex or immunogenic fragments or conjugates thereof. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody.

Antibodies may also be produced by inducing in vivo production in the lymphocyte population or by screening immunoglobulin libraries or panels of highly specific binding reagents as disclosed in the literature (Orlandi, R. et al., *Proc. Natl. Acad. Sci.* 86, 3833–3837 (1989)); Winter, G. et al., (1991) *Nature* 349, 293–299 (1991)).

Antibody fragments that contain specific binding sites for mRNP complexes may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse, W. D. et al. (1989) *Science* 254:1275–1281).

Various immunoassays may be used for screening to identify antibodies having the desired specificity for the mRNP. Numerous protocols for competitive binding or immunoradiometric assays using either polyclonal or monoclonal antibodies with established specificities are well known in the art. Such immunoassays will typically involve the measurement of complex formation between the component of the mRNP complex and its specific antibody. A two-site, monoclonal-based immunoassay utilizing monoclonal antibodies reactive to two non-interfering epitopes is preferred, but a competitive binding assay may also be employed.

Kits or devices (e.g., fluidic devices) containing columns in which antibodies to various mRNP complexes or components thereof (e.g., antibodies to RNA-binding proteins) are immobilized are another aspect of the invention. The antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques. Devices of the present invention will preferably include at least one reagent specific for detecting the binding between an antibody to a mRNA-binding protein and the protein itself. The reagents may also include ancillary agents such as buffering agents and protein stabilizing agents, e.g., polysaccharides and the like. The device may further include, where necessary, agents for reducing background interference in a test, control reagents, apparatus for conducting a test, and the like. The device may be packaged in any suitable manner, typically with all elements in a single container along with a sheet of printed instructions for carrying out the test.

Certain embodiments of the invention relate to methods of screening test compounds for therapeutic, diagnostic or pharmaceutical use, based upon each compound's effect on the ribonomic profile of a cell or tissue sample. In an example of such an embodiment, cells are grown under conditions where the cells have no contact with the test compound (i.e., the cells are not treated). A ribonomic profile of the cell type is then produced, and the mRNA subsets identified. The ribonomic profile of the non-treated cells is then compared to a ribonomic profile of the same cell type that has been treated with the test compound. Any difference between the two profiles is an indication that the test compound has an effect (directly or indirectly) on the expression of certain genes of the cell, and may be an indication that the test compound is a candidate for therapeutic or diagnostic use. Alternatively, the ability of a compound to effect gene expression may identify the gene as a target for further testing. A "difference" in the profiles refers to any modulation or change in expression between the two profiles. "Modulation" can refer to an increase in expression, a decrease in expression, a change in the type or kind of expression present, a complete cessation of expression (i.e., an absence of expression), or the instigation of expression. Suitable compounds that may be used include but are not limited to proteins, nucleic acids, small molecules, hormones, antibodies, peptides, antigens, cytokines, growth factors, pharmacological agents including chemotherapeutics, carcinogenics, or other cells (i.e. cell-cell contacts). Cells may also be screened for the effects of environmental or physiological factors such as radiation, action potentials, etc. on normal gene expression.

In another embodiment of the invention, an mRNP component itself, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The binding between the mRNP complex and the compound being tested may be measured.

Another technique for drug screening which may be used provides for high throughput screening of compounds having suitable binding affinity to the protein of interest as described in published PCT application WO84/03564. In one embodiment, as applied to the mRNP complex, a plurality of different test compounds are synthesized on or affixed to a solid substrate, such as plastic pins or some other surface. The test compounds are reacted with the mRNP complex, or fragments and/or components thereof, and washed. The bound mRNP complex or component thereof is then detected by methods well known in the art.

In summary, the present invention provides powerful in vivo methods for determining the ribonomic profile of a cell and detecting changes in the same. The invention has numerous uses, including but not limited to the monitoring of tumor development, state of growth or state of development, perturbations of a biological system such as disease, drug or toxin treatment, and the state of cell aging or death. The invention also finds use in distinguishing ribonomic profiles amongst organisms such as plant, fungal, bacterial, viral, protozoan, or animal species.

The present invention can be used to discriminate between transcriptional and post-transcriptional contributions to gene expression and to track the movement of RNAs through RNP complexes, including the interactions of combinations of proteins with RNAs in RNP complexes. Accordingly, the present invention can be used to study the regulation of stability of RNAs. The present invention can be used to investigate the activation of translation of mRNAs as single or multiple species by tracking the recruitment of mRNAs to active polysomes, measuring the sequential, ordered expression of mRNAs, and measuring the simultaneous, coordinate expression of multiple mRNAs. The present invention can also be used to determine the trans-acting functions of RNAs themselves upon contacting other cellular components. These and numerous other uses will be made apparent to the skilled artisan upon study of the present specification and claims, The following Examples are set forth to illustrate the present invention, and are not to be construed as limiting thereof.

EXAMPLE 1

RNase Protection in a Multiprobe System: Materials and Methods

It has previously been reported that HuB (Hel-N1) immunoprecipitation, using a g10 epitope tag, resulted in the co-immunoprecipitation of a mRNA, which once amplified by RT-PCR and sequenced, was found to encode NF-M protein (Antic, 1999, supra). In this example, the same approach is expanded to using a multiprobe RNase protection assay to rapidly optimize the immunoprecipitation of several endogenous mRNA-protein (mRNP) complexes containing different mRNA-binding proteins. In the multiprobe system, many mRNAs, from mRNP pellets, can be assayed in a single lane of polyacrylamide gel.

Cell Culture and Transformation Murine P19 embryonal carcinoma cells were obtained from the ATCC and maintained in monolayer culture using $\alpha$-MEM without phenol red (Gibco-BRL 41061–029) supplemented with 7.5% Bovine Calf Serum, 2.5% Fetal Bovine Serum (Hyclone) and 100U Penicillin/Streptomycin. Cells were grown in tissue culture flasks or plates that had been pre-coated with 0.1% gelatin (Sigma Chemicals) that was removed prior to use. Monolayer cell cultures were maintained in 5% $CO_2$ at 37° C.

P19 cells were stably transfected with a SV40 promoter-driven pAlpha2-gene 10-HuB plasmid that ectopically expressed a gene 10-tagged neuron-specific HuB protein termed Hel-N2 (Gao et al. (1994) Proc. Natl. Acad. Sci. USA 91, 11207–11211). The transfected plasmid was maintained by supplementing the medium with 0.2 mg/ml G418 (Sigma Chemicals). Although it lacks thirteen amino acids from the hinge region connecting RNA-recognition motifs (RRMs) 2 and 3 of Hel-N1, the RRMs are identical and in vitro binding experiments have indicated no differences in the AU-rich RNA binding properties of Hel-N1 and Hel-N2 (Gao et al. (1994) Proc. Natl. Acad. Sci. USA 91, 11207–11211; Abe et al. (1996) Nucleic Acids Res. 24, 2011–2016; unpublished results).

Antibodies Monoclonal anti-gene 10 (g10) antibodies were produced as previously described (Gao et al. (1994) Proc. Natl. Acad. Sci. USA 91, 11207–11211; Antic et al. (1999) Genes Dev. 13, 449–461). Polyclonal sera reactive with HuA were produced as previously described (Levine et al. (1993) Mol. Cell. Biol. 13, 3494–3504; Atasoy et al. (1998) J. Cell Sci. 111, 3145–3156). Antibodies reactive with Poly A binding protein (PABP) were kindly provided by Dr. N. Sonenberg of McGill University (Canada).

Preparation of Cell-Free Extracts Cells were removed from tissue culture plates with a rubber scraper and washed with cold PBS. The cells were resuspended in approximately two pellet volumes of polysome lysis buffer (PLB) containing 100 mM KCl, 5 mM $MgCL_2$, 10 mM HEPES pH 7.0, and 0.5% NP-40 with 1 mM DTT, 100 U/mL RNase OUT (GIBCO-BRL), 0.2% vanadyl ribonucleoside complex (VRC)(GIBCO-BRL), 0.2 mM PMSF, 1 mg/mL pepstatin A, 5 mg/mL bestatin, and 20 mg/mL leupeptin added fresh at the time of use. The lysed cells were then frozen and stored at −100° C. At the time of use, the cell lysate was thawed and centrifuged at 12,000 rpm in a tabletop microfuge for 10 min at 4° C. The supernatant was removed and centrifuged a second time at 16,000 rpm in a tabletop microfuge for 5 min at 4° C. before being stored on ice or refrozen at −100° C. The mRNP cell lysate contained approximately 30–50 mg/mL total protein.

Immunoprecipitations For immunoprecipitation, Protein A sepharose beads (Sigma Biochemicals) were swollen 1:5 v/v in NT2 buffer (50 mM Tris pH 7.4, 150 mM NaCl, 1 mM $MgCl_2$, and 0.05% NP-40) supplemented with 5% bovine serum albumin. A 300 µL aliquot of 1:5 v/v pre-swollen Protein A bead slurry was used per immunoprecipitation reaction and incubated overnight at 4° C. with excess immunoprecipitating antibody (typically 5–20 μL, depending on the reagent). The antibody-coated Protein A beads were washed 5 times with ice-cold NT2 buffer and resuspended in 900 μL of NT2 buffer supplemented with 100 U/mL RNase OUT, 0.2% VRC, 1 mM DTT, and 20 mM EDTA. The beads were briefly vortexed and 100 μL of the mRNP cell lysate was added. The beads were immediately centrifuged and 100 μL of the supernatant was removed to represent total cell mRNP lysate (essentially one-tenth the quantity of lysate used in the mRNP immunoprecipitations). The immunoprecipitation reaction and an aliquot removed to represent total cell mRNP lysate were tumbled at room temperature for a time period of from zero time to up to two hours. Following incubation, the Protein A beads were washed four times with ice-cold NT2 buffer followed by two washed with NT2 buffer supplemented with 1 M urea. Washed beads were resuspended in 100 μL NT2 buffer supplemented with 0.1% SDS and 30 μg proteinase K and incubated for 30 min in a 55° C. water bath. Following proteinase K digestion, immunoprecipitated RNA was isolated with two phenol/chloroform/isoamyl alcohol extractions and ethanol precipitated.

RNase Protection Assays After mRNP complexes were immunoprecipitated from cell lysates and the bound RNA extracted, it was assayed by RNase protection using the PharMingen Riboquant assay (San Diego, Calif.) according to the manufacturer's instructions (45014K). Briefly, extracted RNA was hybridized with excess $^{32}$P-labeled riboprobes generated from templates specific for mRNAs encoding L32, GAPDH, several murine Myc-related proteins (template set 45356P) and cyclins (template set 45620P). Non-duplexed RNA was digested by treatment with RNase A+T1. The resulting fragments were resolved by denaturing polyacrylamide/urea gel electrophoresis. Because the length of the riboprobe for each mRNA species was a unique size, all detectable mRNA species in a sample could be resolved in a single gel lane. Protected riboprobe fragments were visualized on a phosphoimaging screen (Molecular Dynamics) after 24 hours of exposure. Phosphoimages were scanned using the Molecular Dynamics STORM 860 System at 100 micron resolution and analyzed using Molecular Dynamics ImageQuant Software (V 1.1).

EXAMPLE 2

RNase Protection in a Multiprobe System: Experimental Results

Figure 1:
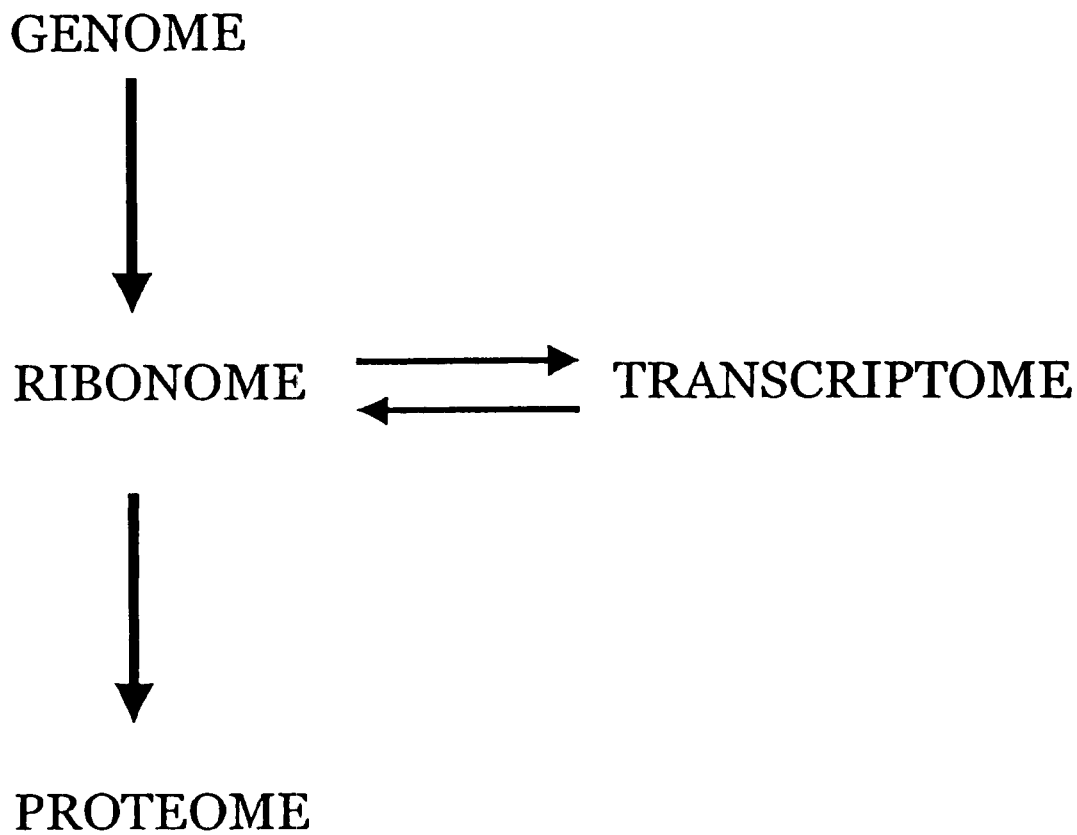
FIG. 1 is a schematic illustrating the flow of genetic information from the genome to the proteome, and the intermediate levels represented by the ribonome and the transcriptome. The transcriptome represents the total mRNA complement of the genome, but does not necessarily correlate directly with protein production. The processing, transport and translation of mRNA occurs in the ribonome, where dynamic regulatory steps determine the proteomic outcome.
Figure 2:
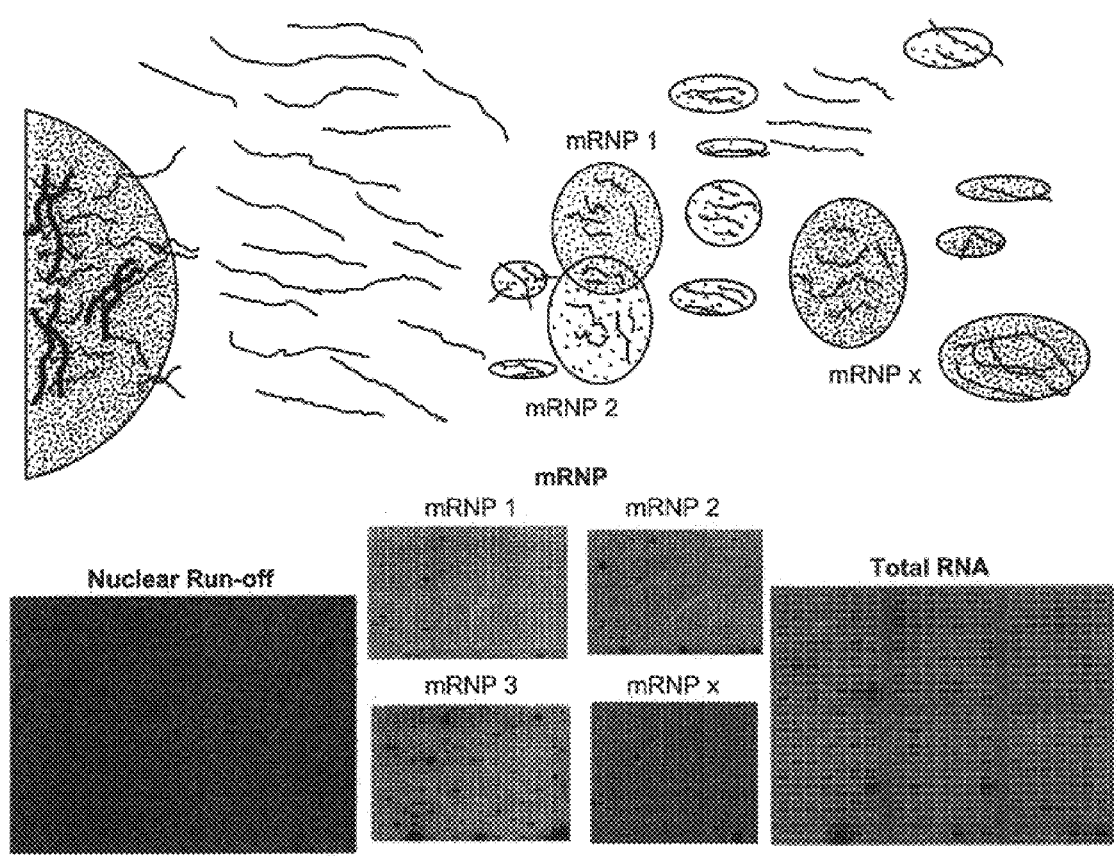
FIG. 2 graphically illustrates a comparison of the total cell mRNA (the transcriptome) with mRNA that has bound within mRNP complexes to form a part of the ribonome. The microarrays representing mRNP complexes contain discrete and more limited subsets of mRNAs, when compared to the transcriptome.
Figure 3A:
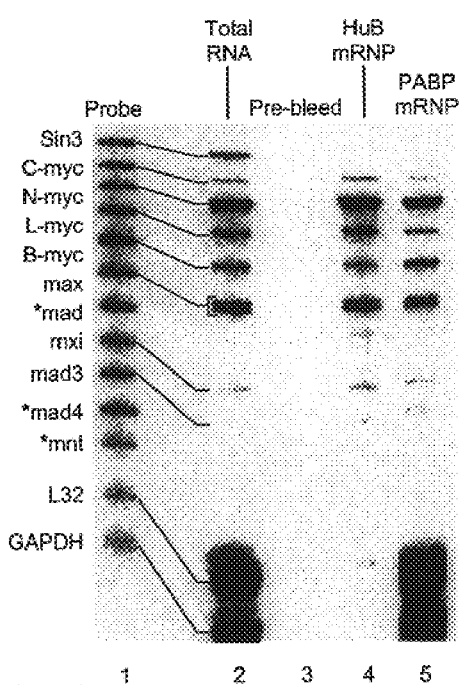
FIGS. 3A and 3B illustrate multi-probe RNase protection analysis of mRNAs associated with mRNP complexes. Messenger RNP complexes from cell lysates were immunoprecipitated, and the pelleted RNA was extracted and quantitated by RNase protection.
Figure 3B:
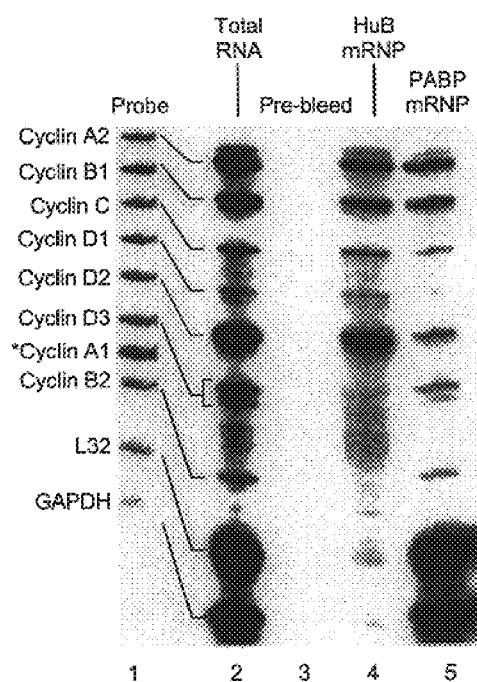

FIG. 3 shows an immunoprecipitation of HuB and Poly-A binding protein (PABP)-mRNP complexes from extracts of murine P19 cells stably transfected with g10-HuB cDNA. No mRNAs were detected in pellets immunoprecipitated with polyclonal pre-bleed rabbit sera (FIG. 3A and 3B, lane 3), or with many other rabbit, mouse, and normal human sera tested with this assay (data not shown). The profiles of mRNAs associated with HuB mRNP complexes included n-myc, 1-myc, b-myc, max and cylins A2, B1, C, D1, and D2, but not sin3, cyclin D3, cyclin B2, L32 or GAPDH mRNAs (FIG. 3A and 3B, lane 4). In contrast, the profiles of mRNAs extracted from PABP-mRNP complexes resembled the profiles of total RNA, but showed enriched levels of L32 and GAPDH and decreased levels of sin3 mRNA (FIG. 3A and 3B, lane 5). It was concluded that antibodies reactive with these cellular RNA-binding proteins could be used to immunoprecipitate mRNP complexes and to recover mRNAs with which they are specifically associated. These results are consistent with the postulate role of Hu proteins in regulating post-transcriptional gene expression during cell growth and differentiation. (Jain et al. (1997) *Mol. Cell. Biol.* 17, 954–962; Levy et al. (1998) *J. Biol. Chem.* 273, 6417–6423; Fan and Steitz (1998) *EMBO J.* 17, 3448–3460; Peng et al. (1998) *EMBO J.* 17, 3461–3470; Antic and Keene (1997)*Am. J. Hum. Genet.* 61, 273–278; Levine et al. (1993) *Mol. Cell Biol.* 13, 3494–3504; Gao et al. (1994) *Proc. Natl. Acad. Sci. USA/* 91, 11207–11211; King et al. (1994) *J. Neurosci.* 14, 1943–1952; Liu et al. (1995) *Neurology* 45, 544–550; Ma et al. (1996) *J. Biol. Chem.* 271, 8144–8151; Abe et al. (1996) *Nucl. Acids Res.* 24, 2011–2016; Antic et al. (1999) *Genes Dev.* 13, 449–461; Chung et al. (1997) *J. Biol. Chem.* 272, 6593–6598; Akamatsu et al. (1999) *Proc. Natl. Acad. Sci. USA* 96, 9884–9890; Sachs et al. (1997) *Cell* 89, 831–838; Aranda-Abreu et al. (1999) *J. Neurosci.* 19, 6907–6917).

EXAMPLE 3

Figure 4:
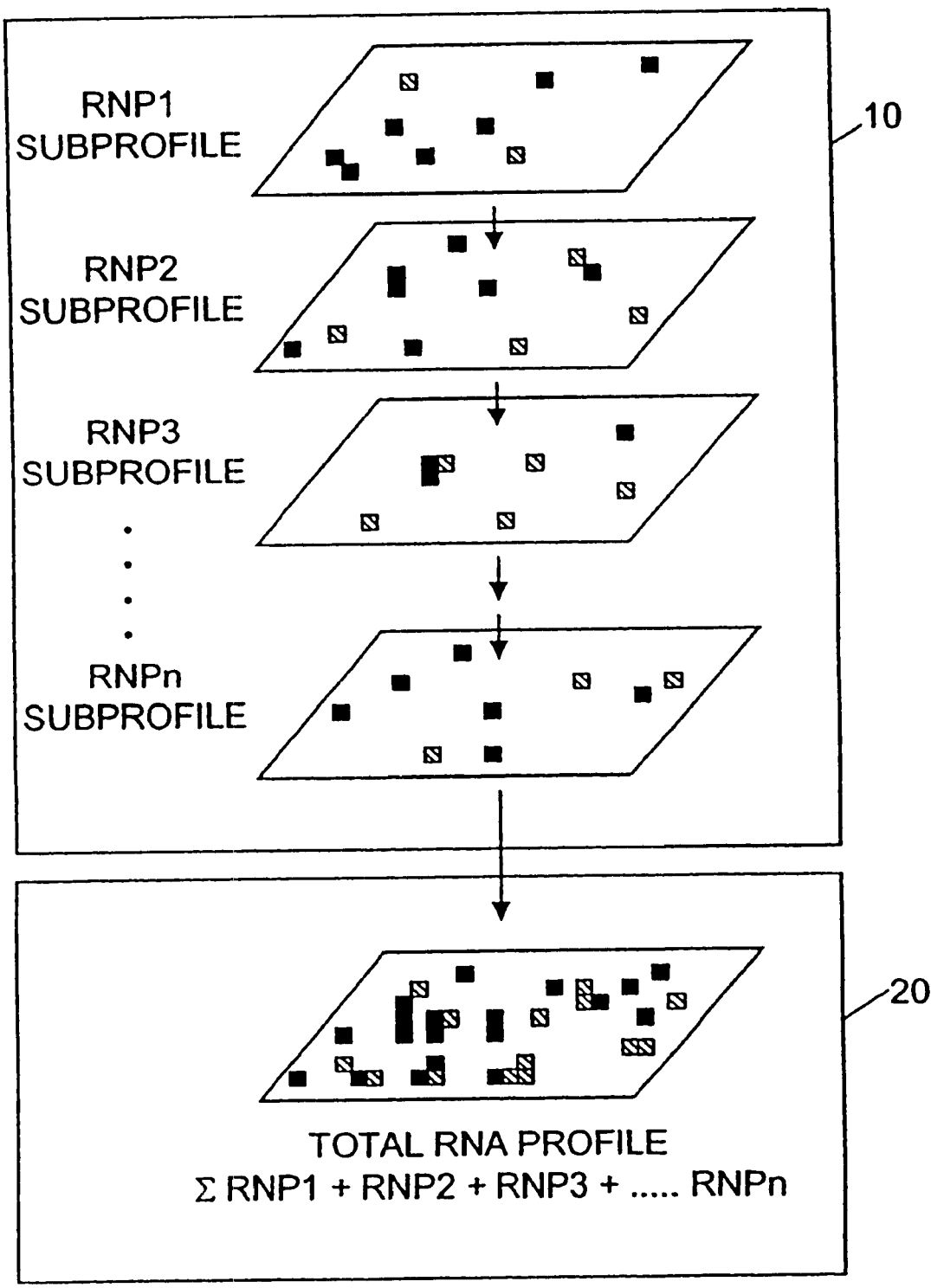
FIG. 4 illustrates ribonome profiling of RNA subsets using DNA arrays. The RNA-protein complexes can be derived from cells of two individuals, species, cell types, treatments, developmental stages, etc. mRNA-protein complexes are separated immunoprecipitations of complexes are conducted, probes are reverse-transcribed from the RNA template, and a DNA array of genes is probed with each pool of RNP-derived probes to generate subprofiles of gene expression (10). Subprofiles are then compared by subtraction or addition to generate an overall picture of gene expression (20). This figure depicts the ribonomic concept, in which different mRNPs are isolated and their associated mRNAs identified using microarrays. The subprofiles (mRNP1, mRNP2, . . . mRNPn) of the total cell profile are shown as additive. Stacked mRNP subprofiles can each represent individual mRNPs within a single cell type, or can represent each individual cell's transcriptome within a complex tissue or tumor.

Identification of mRNA Subsets Associated with RNA Binding Proteins En Masse Using cDNA Arrays: Materials and Methods To further expand the ability to identify the mRNAs associated in endogenous mRNP complexes, this example describes the use of a cDNA array filter as a highly specific and sensitive method to detect a mRNA subset without amplification or iterative selection (FIG. 4).

Antibodies Monoclonal anti-gene 10 (g10) antibodies were produced as previously described (see D. Tsai et al., *Proc. Natl. Acad. Sci. USA,* 89, 8864–8868 (1992); Gao et al. (1994) *Proc. Natl. Acad. Sci. USA* 91, 11207–11211; Antic et al. (1999) *Genes Dev.* 13, 449–461). Polyclonal sera reactive with Hu proteins were produced as previously described (Levine et al. (1993) *Mol. Cell. Biol.* 13, 3494–3504; Atasoy et al. (1998) *J. Cell Sci.* 111, 3145–3156). Antibody against 5' cap binding protein (eIF-4E) was obtained from Transduction Laboratories (San Diego, Calif.). Antibodies reactive with Poly A binding protein (PABP) were kindly provided by Dr. N. Sonenberg of McGill University (Canada).

Cell Culture and Differentiation Preparation of transgenic cells was as described in Example 1. Chemical treatment with retinoic acid (RA) was used to induce neuronal differentiation by treating 5×10$^5$ P19 cells, placed a 60 mm petri dish (Fisher Scientific, Pittsburgh, Pa., USA, Number 8–757–13A), with 0.5 μM RA (Sigma Chemicals, St. Louis, Mo., USA, Number R2625), as described in Gao and Keene (1996)). After two days, 25% of the cells that had formed into clumps were removed, placed in new petri dishes, and supplemented with fresh medium and RA. Following an additional two days, cell aggregates were washed once with phosphate-buffered saline (PBS) and trypsinized. The cells were then plated into two 100 mm gelatin-coated tissue culture plates. Cells were harvested after an additional four days. The RA treated HuB (Hel-N2) stably transfected P19 cells grew neurites and displayed characteristics neuronal markers and morphology, but did not terminally differentiate and remained susceptible to killing with mitotic inhibitors. Cell-free extracts and immunoprecipitations were as described in Example 1.

cDNA Array Analysis cDNA array analysis was performed using Atlas™ Mouse Arrays (Clontech, Inc., Palo Alto, Calif.) that contain a total of 597 cDNA segments spotted in duplicate, side-by-side on a nylon membrane. Probing of cDNA arrays was performed as described in the Clontech Atlas™ cDNA Expression Arrays User Manual (PT3140–1). Briefly, RNA was extracted from HuB stably transfected P19 embryonal carcinoma cells and used to produce reverse transcribed probes. A pooled set of primers, complementary to the genes represented on the array, was used for the reverse transcription probe synthesis, which was radiolabeled with $^{32}$P α-dATP. The radiolabeled probe was purified by passage over CHROMA SPIN™-200 columns (Clontech, Inc., Palo Alto, Calif.) and incubated overnight with an array membrane using ExpressHyb™ hybridization solution (Clontech, Inc., Palo Alto, Calif.). Following hybridization, the array membrane was washed and visualized on a phosphorimaging screen (Molecular Dynamics, Sunnyvale, Calif., USA).

Phosphorimages were scanned using the Molecular Dynamics STORM 860 System at 100 micron resolution and stored as files. Images were analyzed using AtlasImage™ 1.0 and 1.01 software (Clontech, Inc., Palo Alto, Calif.). The signal for any given gene was calculated as the average of the signals from the two duplicate cDNA spots. As described in the AtlasImage™ 1.0 software manual (Clontech, Inc., Palo Alto, Calif.), a default external background setting was used in conjunction with a background-based signal threshold to determine gene signal significance. The signal for a gene was considered significantly above background if its adjusted intensity (total signal minus background) was more then two-fold the background signal. Comparisons of multiple cDNA array images were performed using an average of all the gene signals on the array (global normalization) to normalize the signal intensity between arrays. Changes in the mRNA profile of HuB mRNP complexes in response to retinoic acid treatment were considered significant if they were four-fold greater (twice the stringency typically used for establishing significance of a gene expression change). cDNA array images and overlays were prepared using Adobe Photoshop® 5.0.2 (San Jose, Calif., USA).

EXAMPLE 4

Identification of mRNA Subsets Associated with RNA Binding Proteins En Masse Using cDNA Arrays: Experimental Results Results After assessing the overall gene expression profile of HuB transfected P19 cells (the transcriptome), HuB and PABP mRNA complexes, as well as elF-4E mRNP complexes were separately immunoprecipitated and captured mRNAs were identified on cDNA arrays. The initial alignment of these arrays was facilitated by spiking the hybridization reaction with radiolabeled lambda phage markers that hybridized with six DNA spots on the bottom of the array membrane. Once the alignment register was established, subsequent blots did not require the use of spiked lambda markers for orientation.

Figure 5D:
FIG. 5 (parts A–E) sets forth the results of illustrative Example 4, below, and shows mRNAs associated with mRNP complexes using cDNA arrays. Panels: (A) pre-bleed; (B) HuB mRNP complexes; (C) elF-4E mRNP complexes; (D) PABP mRNP complexes; (E) total cellular RNA. An example of the specificity of the procedure is indicated by the differential abundance of the mRNAs encoding β-actin and ribosomal protein S29 among the mRNP profiles (arrows a and b, respectively). Other examples of such specificity are readily observable with other mRNAs (data not shown).
Figure 5B:
Figure 5E:
Figure 5C:

Arrays generated from immunoprecipitations with rabbit pre-bleed sera were essentially blank with the exception of the spiked lambda markers observed at the bottom of the array (FIG. 5A). Immunoprecipitated HuB mRNP and elF-4E mRNP complexes each contained slightly more than 10% of the mRNAs detected in total cell RNA, but differed considerably from one another (FIG. 5B, 5C, and 5E).

Like HuB and elF-4E, PABP has been implicated in facilitating mRNA stabilization and translation (Ross (1995) *Microbiol. Rev.* 59, 423–450; Ross (1996) *Trends Genet.* 12, 171–175; Wickens et al. (1996) in *Translational control,* eds Hershey, J. W. B, Mathews, M. B. & Sonenberg, N., Cold Spring Harbor Laboratory Press, Cold Spring Harbor, pp. 411–450; Sachs et al. (1997) *Cell* 89, 831–838). Not surprisingly, PABP mRNPs contained many more detectable mRNAs than those observed in the HuB or elF-4E mRNPs (FIG. 5D). As expected, the profile of the mRNAs in the PABP mRNPs from these cells closely resembled that of the transcriptome. However, as was seen for HuB and elF-4E mRNPs, some mRNAs were enriched or depleted in the PABP-mRNPs as compared to the total RNA (FIG. 5D and 5E). The profiles and relative abundance of mRNAs detected in these mRNP complexes were highly reproducible, but the absolute number of mRNA species detectable on the phosphorimages occasionally varied as a result of differences in the specific activity of the probe.

Because the cDNA arrays derived using total RNA were generated using one-tenth the quantity of lysate used for mRNP immunoprecipitations, a comparison of the absolute quantities of each mRNA detected in mRNP complexes with those observed in the total RNA was not conducted. A more accurate result was obtained by comparing the relative abundance of each mRNA species to each other within each microarray. For example, the relative abundance of the mRNA encoding β-actin and ribosomal protein S29 (FIG. 5, arrows a and b, respectively) are approximately equal to the total cellular RNA, but varied dramatically among each of the mRNP complexes. Many other examples of this distinction are readily apparent in FIG. 4. These findings indicated that the mRNA profiles detected in HuB, elF-4E, and PABP mRNP complexes are distinct from one another and from those of the transcriptome.

EXAMPLE 5

Alterations in mRNP Complexes in Response to Retinoic Acid (RA)

Figures 6A, 6B, 6C:
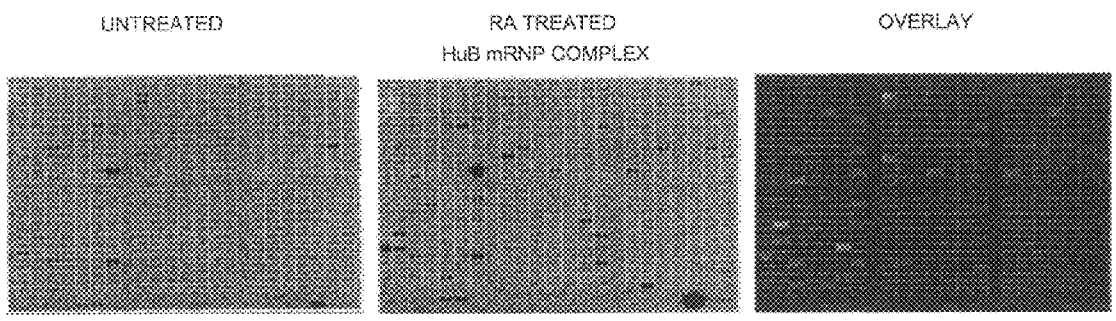
FIG. 6 (parts A–I) sets forth the results of illustrative Example 5, below, and shows a comparison of the mRNA profiles from HuB mRNPs before and after treatment with retinoic acid (RA). Panels: (A) mRNAs extracted from HuB mRNPs immunoprecipitated from untreated cells; (B) mRNAs extracted from HuB mRNPs immunoprecipitated from RA-treated cells; (C) a computer-generated comparison of panels A and B; (D) mRNAs extracted from HuA (HuR) mRNPs immunoprecipitated from untreated cells; (E) mRNAs extracted from HuA mRNPs immunoprecipitated from RA-treated cells; (F) a computer-generated comparison of panels D and E; (G) total complement of mRNAs extracted from untreated cellular lysate; (H) total complement of mRNAs extracted from RA-treated cellular lysate; and (I) a computer-generated comparison of panels G and H.

Since HuB is predominantly a neuronal protein believed to play a role in regulating neuronal differentiation, studies were conducted to investigate whether the mRNA population found in HuB mRNP complexes changes in response to RA, a chemical inducer of neuronal differentiation. HuB transfected P19 cells were treated with RA to induce the onset of neuronal differentiation, HuB mRNP complexes were immunoprecipitated, and then associated mRNAs were identified on cDNA arrays. Comparison of the mRNA profiles extracted from the HuB mRNPs before and after RA treatment revealed that eighteen mRNAs were either exclusively present or greatly enriched (four-fold or greater) in RA-treated HuB mRNPs (FIG. 6A, 6B, and 6C, red bars). In addition, three mRNAs (T-lymphocyte activated protein, DNA-binding protein SATB1, and HSP84) decreased in abundance by four-fold or greater in response to RA treatment (FIG. 6C, blue bars). To determine if the changes observed in the mRNA profile of the HuB mRNA complexes were unique, the ubiquitously expressed ELAV family member HuA (HuR) was immunoprecipitated from these RA treated cells. Although there were a few changes to the HuA mRNP profile following treatment with RA, they were minor in comparison with HuB.

The changes in the HuB-associated mRNA profile in response to RA treatment did not merely reflect changes in the total cellular mRNA (FIG. 6G, 6H, and 6I). Numerous examples of differentially-enriched or depleted mRNAs detected in HuB mRNP complexes are evident by comparing FIG. 6C and 6I. For comparative purposes, this is depicted in FIG. 7 by realignment and enlargement of representative spots. For example, IGF-2 mRNA was detectable only in total RNA and HuB mRNP complexes from RA-treated cells (FIG. 7). However, other HuB-mRNP-bound mRNAs, such as integrin beta, cyclin D2, and Hsp84 increased or decreased in abundance disproportionately to their changes in the total RNA profile following RA treatment (FIG. 7). The disparity between changes in the mRNA profiles of total RNA and HuB mRNPs possibly results from changes in compartmentalization of mRNAs that flux dynamically through mRNP complexes in response to RA treatment. It can be concluded that the mRNA profiles derived from these mRNP complexes are dynamic and can reflect the state of growth, as well as changes in the cellular environment in response to a biological inducer like retinoic acid.

EXAMPLE 6

In vivo Target Sequence Preferences For RNA-Binding Proteins

Using GenBank and EST databases, the 3' UTR sequences from mRNAs enriched in RA-treated HuB-mRNP complexes were identified (TABLE 2).

(Beck et al. (1995) *Neuron* 14, 717–730; Colon and Rossant (1992) *Development* 116, 357–368; Graham et al. (1991) *Development* 112, 255–264; Hirsch et al. (1994) *Dev. Dyn.* 201, 108–120; Hunt et al. (1991) *Development* 112, 43–50; Janssen-Timmen et al. (1989) *Gene* 80, 325–336; Kondo et al. (1992) *Nucleic Acids Res.* 20, 5729–5735; Konishi et al. (1994) *Brain Res.* 649, 53–61; Neuman et al. (1993) *Eur. J. Neurosci.* 5, 311–318; Okuda et al. (1995) *Genomics* 29, 623–630; Soosaar et al. (1994) *Bran Res. Mol. Brain Res.* 25, 176–180; Takechi et al. (1992) *Eur. J. Biochem.* 206, 323–329; Telford et al. (1990) *Mol. Reprod. Dev.* 27, 81–92; Zwartkrius et al. (1993) *Exp. Cell Res.* 205, 422–425; Tomaselli et al. (1988) *Neuron* 1, 33–43; Redies (1995) *Exp. Cell Res.* 220, 243–256; Ross et a. (1996) *J. Neurosci.* 16, 210–219). The sequence alignment shown in TABLE 3 is consistent with the previous results of Levine et al. ((1993) *Mol. Cell Biol.* 13, 2494–3504) and Gao et al. ((1994) *Proc. Natl. Acad. Sci. USA* 91, 11207–11211) who used in vitro selection to derive a consensus RNA-binding sequence for

TABLE 2

| Gene | #'UTR Consensus Sequence |
| --- | --- |
| CD44 | AUUUUCUAUUCCUUU<u>UUUAUUU</u> UAUGUCAUUUUUUUA [SEQ ID NO: 1] |
| IGF-2 | UAAAAAACCAAA<u>UUUGAUU</u> GGCUCUAAACA [SEQ ID NO: 2] |
|  | UAAAGAA<u>AUUAAUU</u> GGCUAAAAACAUA [SEQ ID NO: 3] |
|  | CUAAAA<u>AUUAAUU</u> GGCUUAAAAA [SEQ ID NO: 4] |
| HOX 2.5 | UCACUCUU<u>AUUAUUU</u> AU [SEQ ID NO: 5] |
|  | AAAU<u>UUUAUUA</u> AGUUA [SEQ ID NO: 6] |
|  | AUCAGG<u>UUCAUUU</u> UGGUUGU [SEQ ID NO: 7] |
| Inhibitor | AU<u>UUUAUCU</u> GUUA [SEQ ID NO: 8] |
| J6 | UUUUGUUUUUCUCCCUUUU<u>UUAGUUU</u> UUUCAAA [SEQ ID NO: 9] |
| GADD45 | UAUUUUUUUUCUUUUUUUU<u>UUUUGGU</u> CUUUAU [SEQ ID NO: 10] |
|  | UUAAAUUCUCAGAAGU<u>UUUAUUA</u> UAAAUCUU [SEQ ID NO: 11] |
| Nexin 1 | UUCUGUUAAAUAUU<u>UUUAUAU</u> ACUGCUUUCUUUUUU [SEQ ID NO: 12] |
|  | AUUUUAUAGUAGUU<u>UUUAUGU</u> UUUUAUGGAAAA [SEQ ID NO: 13] |
|  | AUUUGCCUU<u>UUUAAUU</u> CUUUUU [SEQ ID NO: 14] |
| Egr-1 | UAUUUUGUGGU<u>UUUAUUU</u> UACUUUGUACUU [SEQ ID NO: 15] |
| Zif268 | U<u>UUUGUUU</u> UCCUU [SEQ ID NO: 16] |
| Neuronal- | UU<u>UUUUAUUU</u> UCUGUAUUUUUU [SEQ ID NO: 17] |
| Cadherin | UUUUUUUUAAAUUUU<u>UUUAUUU</u> UCUUUUU [SEQ ID NO: 18] |
|  | UUUUUUAUUUUC<u>UGUAUUU</u> UUU [SEQ ID NO: 19] |
|  | UUUUUAAUUU<u>UUUAAUU</u> UUUUUU [SEQ ID NO: 20] |
| Integrin | AAUGG<u>UUUAUAU</u> UUAUGAU [SEQ ID NO: 21] |
| alpha 5 | UUG<u>UUUAUAU</u> CUUCAAU [SEQ ID NO: 22] |
| SEF2 | UUCAAGCGC<u>UUGANUU</u> [SEQ ID NO: 23] |
| Cf2r | UGCAUCGAUCCG<u>UUGAUUU</u> ACUACU [SEQ ID NO: 24] |
| Integrin | UAUAAUUU<u>UUAAUUU</u> UUUAUUAUUUU [SEQ ID NO: 25] |
| Beta | UUAUUUUACCUUUUUUUUUUUUC<u>UUUAAUU</u> CCUGGU [SEQ ID NO: 26] |
| CTCF | UUAUGAAUGU<u>UAUAUUU</u> GU [SEQ ID NO: 27] |
|  | UC<u>UUAAUUU</u> UUUCUCUUUUUUUUCUUU [SEQ ID NO: 28] |
| TGF beta 2 | UUUUUUUUUCC<u>UUUUAAUU</u> GUAAAUGGUUCUUU [SEQ ID NO: 29] |
|  | UUAAUGAUCAUUCAGAUUGUA<u>UAUAUUU</u> GUUUCCUUU [SEQ ID NO: 30] |
|  | UUCAAUUUUU<u>UUUAUAU</u> ACUAUCUU [SEQ ID NO: 31] |
|  | UUUUUC--<u>UUUAAUU</u> GGUUUUUUU [SEQ ID NO: 32] |
| MTP | UGUCUUGUCUGAGCA<u>UUUAUUU</u> UCAAA [SEQ ID NO: 33] |
|  | UUCUCGUCUUG<u>UUUAUUU</u> UACAA [SEQ ID NO: 34] |
|  | UAUAAUAAUAG<u>UUUAUGU</u> UUUGGAUGUUUGGU [SEQ ID NO: 35] |
| Cyclin D2 | AUGUCUUGUUCUU<u>UGUGUUU</u> UUAGGAU [SEQ ID NO: 36] |
|  | (AU/GA)<u>UUUAUUU</u> (UA/AG) [SEQ ID NO: 37] |
|  | In Vitro Consensus Sequence |

Many of the mRNAs for which 3' UTR sequences were available contained similar uridylate-rich motifs as those previously found to bind to Hu protein in vitro (Levine et al. (1993) *Mol. Cell Biol.* 13, 3494–3504; Gao et al. (1994) *Proc. Natl. Acad. Sci. USA* 91, 11207–11211; King et al (1994) *J. Neurosci.* 14, 1943–1952; Liu et al. (1995) *Neurology* 45, 544–550; Ma et al. (1997) *Nucleic Acids Res.* 25, 3564–3569; Fan et al. (1997) *Genes Dev.* 11, 2557–2568). Moreover, most of these mRNAs encode proteins that are expressed in neuronal tissues or are known to be up-regulated following RA-induced neuronal differentiation HuB. Using the methods described herein, it is possible to discern in vivo target sequence preferences for other RNA-binding proteins.

EXAMPLE 7

Use Of mRNA Binding Proteins To Purify Endogenous mRNP Complexes And To Identify Associated mRNAs En Masse Using cDNA Array Analysis Earlier attempts to identify mRNA targets of the HuB protein using high-throughput methods required RT-PCR amplification and in vitro iterative selection and identified several structurally related ERG mRNAs from neuronal tissues (Gao et al. (1994) Proc. Natl. Acad. Sci. USA 91, 11207–11211; Andrews and Keene (1999) Methods Mol. Biol. 118, 233–244). Most of these mRNAs contained ARE-like sequences in their 3'-UTRs, which is a characteristic of ERG mRNAs (Keene (1999) Proc. Natl. Acad. Sci. USA 96, 5–7; Levine et al. (1993) Moll. Cell Biol. 13, 3494–3504; Gao et al. (1994) Proc. Natl. Acad. Sci. USA 91, 11207–11211; King et al. (1994) J. Neurosci. 14, 1943–1952). It has been demonstrated that Hu proteins can bind ERG mRNAs and affect their stability and/or translational activation (Jain et al. (1997) Mol. Cell Biol. 17, 954–962; Levy et al. (1998) J. Biol. Chem. 273, 6417–6423; Fan and Steitz (1998) EMBO J. 17, 3448–3460; Peng et al. (1998) EMBO J. 17, 3461–3470; Keene (1999) Proc. Natl. Acad. Sci. USA 96, 5–7; Levine et al. (1993) Mol. Cell Biol. 13, 3494–3504; Gao et al. (1994) Proc. Natl. Acad. Sci. USA 91, 11207–11211; King et al. (1994) J. Neurosci. 14, 1943–1952; Liu et al. (1995) Neurology 45, 544–550; Chung et al. (1997) J. Biol. Chem. 272, 6593–6598; Antic et al. (1999) Genes Dev. 13, 449–461; Ma et al. (1997) Nucleic Acids Res. 25, 3564–3569; Aranda-Abreu et al. (1999) J. Neurosci. 19, 6907–6917). The in vitro approach of Gao et al. ((1994) Proc. Natl. Acad. Sci. USA 91, 11207–11211) yielded a distinct mRNA subset from human brain and medulloblastoma cells with ERG sequence characteristics. This more direct in vivo approach obviates the need for in vitro binding and PCR amplification. Moreover, this new approach allows the identification of mRNA transcripts with linked structural and functional properties, may of which would not be detected (and could not be detected) using in vitro techniques. In addition, recognizable HuB protein-RNA binding sequences were identified within the in vivo-captured mRNA subset (TABLE 2).

The foregoing examples are illustrative of the present invention, and are not to be construed as limiting thereof. The invention is described by the following claims, with equivalents of the claims to be included therein.

That which is claimed is:

1. A method of generating a gene expression profile of mRNA in a cell in vivo, comprising the steps of:
   partitioning from a cell at least one mRNA-protein (mRNP) complex comprising at least one mRNA bound to or associated with a protein, the step of partitioning comprising:
      contacting a biological sample comprising a mRNP complex from the cell with at least one ligand that specifically binds at least one component of the mRNP complex;
      separating the mRNP complex by binding the ligand with an antibody specific for the ligand, wherein the antibody is attached to a solid support; and
      collecting the mRNP complex by removing the mRNP complex from the solid support; and
   identifying the mRNA in the mRNP complex, thereby to produce a gene expression profile comprising the identity of the mRNA in the mRNP complex.

2. The method according to claim 1, wherein the biological sample comprises a cell culture or a cell extract.

3. The method according to claim 1, wherein the biological sample comprises whole tissue.

4. The method according to claim 1, wherein the biological sample comprises a whole organ.

5. The method according to claim 1, wherein the biological sample comprises a tumor.

6. The method according to claim 1, wherein the biological sample comprises a tumor cell or a tumor cell extract.

7. The method according to claim 1, wherein the biological sample comprises a population of neurons.

8. The method according to claim 1, wherein the component of the mRNP complex is nucleic acid.

9. The method according to claim 1, wherein the component of the mRNP complex is RNA.

10. The method according to claim 1, wherein the component of the mRNP complex is mRNA.

11. The method according to claim 1, wherein the component of the mRNP complex is mature mRNA.

12. The method according to claim 1, wherein the component of the mRNP complex is a RNA-binding protein.

13. The method according to claim 1, wherein the component of the mRNP complex is a RNA-associated protein.

14. The method according to claim 1, wherein the component of the mRNP complex is selected from the group consisting of carbohydrates, lipids, and vitamins.

15. The method according to claim 1, comprising identifying the mRNA bound or associated in the mRNP complex by separating the mRNA from the mRNP complex, obtaining a cDNA of the mRNA and then sequencing the cDNA.

16. The method according to claim 1, comprising identifying the mRNA on a microarray.

17. The method according to claim 1, wherein the ligand is an ELAV/Hu protein selected from the group consisting of HuA, HuB, HuC and HuD.

18. The method according to claim 1, wherein the ligand is an antibody specific for the at least one component of the mRNP complex, and the mRNP complex is separated by immunoprecipitation.

19. The method according to claim 1, wherein a plurality of ligands is contacted with the biological sample to isolate the mRNP complexes.

20. The method according to claim 1, further comprising the step of cross-linking the mRNP complex prior to contacting the mRNP complex with the ligand.

21. The method according to claim 1, further comprising the step of cross-linking the ligand with the mRNP complex after contacting the mRNP complex with the ligand.

22. The method according to claim 1, wherein the at least one mRNA bound to or associated with the protein comprises a subset of the mRNA of the cell and further comprising the step of identifying the mRNA subset for the at least one mRNP complex, thereby to produce the gene expression profile further comprising the identity of the mRNA subset.

23. The method according to claim 1, wherein the step of partitioning from the cell the at least one mRNA-protein (mRNP) complex comprises partitioning from the cell a plurality of mRNP complexes en masse.

24. The method according to claim 1, wherein the step of partitioning from the cell the at least one mRNA-protein (mRNP) complex comprises partitioning from the cell a plurality of mRNP complexes sequentially.

25. The method according to claim 1, comprising the step of isolating each of the at least one mRNP complex prior to identifying the mRNA in the mRNP complex.

26. A method of generating a gene expression profile of the mRNA in a cell in vivo comprising the steps of:
   isolating a plurality of mRNA-protein (mRNP) complexes from a cell, wherein each of the mRNP complexes comprises at least one mRNA bound to or associated with a protein, the step of isolating comprising:
      contacting the plurality of mRNP complexes from the cell with at least one ligand that binds to at least one component of the each of the mRNP complexes, wherein the ligand is attached to a solid support, and
      separating the mRNP complexes from the at least one ligand to isolate the mRNP complexes; and
   identifying each of the mRNAs in the mRNP complexes, thereby to produce a gene expression profile comprising the identities of the mRNAs in the mRNP complexes.

27. The method according to claim 26, wherein the at least one mRNA bound to or associated with the protein comprises a subset of the mRNA of the cell and further comprising the step of identifying the mRNA subset for the plurality of mRNP complexes, thereby to produce the gene expression profile further comprising the identity of the mRNA subset.

28. The method according to claim 26, wherein said isolating step comprises producing a cell extract.

29. The method according to claim 26, wherein said cell is a tumor cell.

30. The method according to claim 26, wherein said cell is a neuronal cell.

31. The method according to claim 26, wherein said ligand is an antibody.

32. The method according to claim 26, wherein said ligand is an antibody isolated using the serum of a subject with cancer.

33. The method according to claim 26, wherein said ligand is an antibody isolated using the serum of a subject with an autoimmune disorder.

34. The method according to claim 26, wherein said component is a nucleic acid.

35. The method according to claim 26, wherein said component is RNA.

36. The method according to claim 26, wherein said component is mRNA.

37. The method according to claim 26, wherein said component is mature mRNA.

38. The method according to claim 26, wherein said component is an RNA-binding protein.

39. The method according to claim 26, wherein said component is an RNA-associated protein.

40. The method according to claim 26, wherein said component is selected from the group consisting of carbohydrates, lipids and vitamins.

41. The method according to claim 26, wherein said identifying step comprises placing said at least one mRNA on a microarray.

42. The method according to claim 26, wherein the ligand is an ELAV/Hu protein selected from the group consisting of HuA, HuB, HuC and HuD.

43. The method according to claim 26, wherein the ligand is an antibody specific for said component.

44. The method according to claim 26, wherein said separating step comprises immunoprecipitation of said mRNP complexes.

45. The method according to claim 26, further comprising the step of cross-linking the mRNP complexes prior to contacting the mRNP complexes with the ligand.

46. The method according to claim 26, further comprising the step of cross-linking the ligand with the mRNP complexes after contacting the mRNP complexes with the ligand.

47. The method according to claim 26, wherein said partitioning step comprises partitioning from the cell the plurality of mRNP complexes en masse.

48. The method according to claim 26, wherein said partitioning step comprises partitioning from the cell the plurality of mRNP complexes sequentially.

49. The method according to claim 26, wherein said isolating step comprises isolating each of the mRNP complexes prior to identifying the mRNA in the mRNP complexes.

* * * * *

SEQUENCE LISTING

```
<160> NUMBER OF SEQ ID NOS: 37

<210> SEQ ID NO 1
<211> LENGTH: 37
<212> TYPE: RNA
<213> ORGANISM: Artificial Sequence
<220> FEATURE:
<223> OTHER INFORMATION: 3'-UTR sequence of CD44

<400> SEQUENCE: 1
auuuucuauu ccuuuuuuau uuuaugucau uuuuuua                    37

<210> SEQ ID NO 2
<211> LENGTH: 30
<212> TYPE: RNA
<213> ORGANISM: Artificial Sequence
<220> FEATURE:
<223> OTHER INFORMATION: 3'-UTR sequence of IGF-2

<400> SEQUENCE: 2
uaaaaaacca aauuugauug gcucuaaaca                            30

<210> SEQ ID NO 3
<211> LENGTH: 27
<212> TYPE: RNA
<213> ORGANISM: Artificial Sequence
<220> FEATURE:
<223> OTHER INFORMATION: 3'-UTR sequence of IGF-2

<400> SEQUENCE: 3
uaaagaaauu aauuggcuaa aaacaua                               27

<210> SEQ ID NO 4
<211> LENGTH: 23
<212> TYPE: RNA
<213> ORGANISM: Artificial Sequence
<220> FEATURE:
<223> OTHER INFORMATION: 3'-UTR sequence of IGF-2

<400> SEQUENCE: 4
cuaaaaauua auuggcuuaa aaa                                   23
```

```
<210> SEQ ID NO 5
<211> LENGTH: 17
<212> TYPE: RNA
<213> ORGANISM: Artificial Sequence
<220> FEATURE:
<223> OTHER INFORMATION: 3'-UTR sequence of HOX 2.5

<400> SEQUENCE: 5
ucacucuuau uauuuau                                                    17

<210> SEQ ID NO 6
<211> LENGTH: 16
<212> TYPE: RNA
<213> ORGANISM: Artificial Sequence
<220> FEATURE:
<223> OTHER INFORMATION: 3'-UTR sequence of HOX 2.5

<400> SEQUENCE: 6 aaauuuauu aaguua                                                      16

<210> SEQ ID NO 7
<211> LENGTH: 20
<212> TYPE: RNA
<213> ORGANISM: Artificial Sequence
<220> FEATURE:
<223> OTHER INFORMATION: 3'-UTR sequence of HOX 2.5

<400> SEQUENCE: 7
aucagguuca uuuugguugu                                                 20

<210> SEQ ID NO 8
<211> LENGTH: 13
<212> TYPE: RNA
<213> ORGANISM: Artificial Sequence
<220> FEATURE:
<223> OTHER INFORMATION: 3'-UTR sequence of Inhibitor J6

<400> SEQUENCE: 8
auuuuaucug uua                                                        13

<210> SEQ ID NO 9
<211> LENGTH: 33
<212> TYPE: RNA
<213> ORGANISM: Artificial Sequence
<220> FEATURE:
<223> OTHER INFORMATION: 3'-UTR sequence of Inhibitor J6

<400> SEQUENCE: 9
uuuuguuuuu cucccuuuuu uaguuuuuc aaa                                   33

<210> SEQ ID NO 10
<211> LENGTH: 32
<212> TYPE: RNA
<213> ORGANISM: Artificial Sequence
<220> FEATURE:
<223> OTHER INFORMATION: 3'-UTR sequence of GADD45

<400> SEQUENCE: 10 uauuuuuuu cuuuuuuuu uuuggucuuu au                                     32

<210> SEQ ID NO 11
<211> LENGTH: 31
<212> TYPE: RNA
<213> ORGANISM: Artificial Sequence
<220> FEATURE:
<223> OTHER INFORMATION: 3'-UTR sequence of GADD45
```

```
<400> SEQUENCE: 11
uuaaauucuc agaaguuuua uuauaaaucu u                                31

<210> SEQ ID NO 12
<211> LENGTH: 36
<212> TYPE: RNA
<213> ORGANISM: Artificial Sequence
<220> FEATURE:
<223> OTHER INFORMATION: 3'-UTR sequence of Nexin 1

<400> SEQUENCE: 12
uucuguuaaa uauuuuaua uacugcuuuc uuuuuu                            36

<210> SEQ ID NO 13
<211> LENGTH: 33
<212> TYPE: RNA
<213> ORGANISM: Artificial Sequence
<220> FEATURE:
<223> OTHER INFORMATION: 3'-UTR sequence of Nexin 1

<400> SEQUENCE: 13
auuuuauagu aguuuuaug uuuuuaugga aaa                               33

<210> SEQ ID NO 14
<211> LENGTH: 22
<212> TYPE: RNA
<213> ORGANISM: Artificial Sequence
<220> FEATURE:
<223> OTHER INFORMATION: 3'-UTR sequence of Nexin 1

<400> SEQUENCE: 14
auuugccuuu uuaauucuuu uu                                          22

<210> SEQ ID NO 15
<211> LENGTH: 30
<212> TYPE: RNA
<213> ORGANISM: Artificial Sequence
<220> FEATURE:
<223> OTHER INFORMATION: 3'-UTR sequence of Egr-1

<400> SEQUENCE: 15
uauuuugugg uuuuauuuua cuuuguacuu                                  30

<210> SEQ ID NO 16
<211> LENGTH: 13
<212> TYPE: RNA
<213> ORGANISM: Artificial Sequence
<220> FEATURE:
<223> OTHER INFORMATION: 3'-UTR sequence of Zif 268

<400> SEQUENCE: 16 uuuuguuuc cuu                                                     13

<210> SEQ ID NO 17
<211> LENGTH: 22
<212> TYPE: RNA
<213> ORGANISM: Artificial Sequence
<220> FEATURE:
<223> OTHER INFORMATION: 3'-UTR sequence of Neuronal-Cadherin

<400> SEQUENCE: 17
uuuuuuauuu ucuguauuuu uu                                          22

<210> SEQ ID NO 18
<211> LENGTH: 29
```

```
<212> TYPE: RNA
<213> ORGANISM: Artificial Sequence
<220> FEATURE:
<223> OTHER INFORMATION: 3'-UTR sequence of Neuronal-Cadherin

<400> SEQUENCE: 18
uuuuuuuuaa auuuuuuuau uuucuuuuu                                        29

<210> SEQ ID NO 19
<211> LENGTH: 22
<212> TYPE: RNA
<213> ORGANISM: Artificial Sequence
<220> FEATURE:
<223> OTHER INFORMATION: 3'-UTR sequence of Neuronal-Cadherin

<400> SEQUENCE: 19
uuuuuuauuu ucuguauuuu uu                                               22

<210> SEQ ID NO 20
<211> LENGTH: 23
<212> TYPE: RNA
<213> ORGANISM: Artificial Sequence
<220> FEATURE:
<223> OTHER INFORMATION: 3'-UTR sequence of Neuronal-Cadherin

<400> SEQUENCE: 20
uuuuuaauuu uuuaauuuuu uuu                                              23

<210> SEQ ID NO 21
<211> LENGTH: 19
<212> TYPE: RNA
<213> ORGANISM: Artificial Sequence
<220> FEATURE:
<223> OTHER INFORMATION: 3'-UTR sequence of integrin alpha 5

<400> SEQUENCE: 21 aauguuuau auuuaugau                                                    19

<210> SEQ ID NO 22
<211> LENGTH: 17
<212> TYPE: RNA
<213> ORGANISM: Artificial Sequence
<220> FEATURE:
<223> OTHER INFORMATION: 3'-UTR sequence of integrin alpha 5

<400> SEQUENCE: 22
uuguuuauau cuucaau                                                     17

<210> SEQ ID NO 23
<211> LENGTH: 16
<212> TYPE: RNA
<213> ORGANISM: Artificial Sequence
<220> FEATURE:
<223> OTHER INFORMATION: 3'-UTR sequence of SEF2
<220> FEATURE:
<221> NAME/KEY: misc_feature
<222> LOCATION: (14)..(14)
<223> OTHER INFORMATION: wherein n at position 14 is a U, G, C or A

<400> SEQUENCE: 23
uucaagcgcu uganuu                                                      16

<210> SEQ ID NO 24
<211> LENGTH: 25
<212> TYPE: RNA
<213> ORGANISM: Artificial Sequence
<220> FEATURE:
```

<223> OTHER INFORMATION: 3'-UTR sequence of Cf2r

<400> SEQUENCE: 24
ugcaucgauc cguugauuua cuacu                                    25

<210> SEQ ID NO 25
<211> LENGTH: 26
<212> TYPE: RNA
<213> ORGANISM: Artificial Sequence
<220> FEATURE:
<223> OTHER INFORMATION: 3'-UTR sequence of integrin beta

<400> SEQUENCE: 25
uauaauuuuu aauuuuuuau uauuuu                                   26

<210> SEQ ID NO 26
<211> LENGTH: 36
<212> TYPE: RNA
<213> ORGANISM: Artificial Sequence
<220> FEATURE:
<223> OTHER INFORMATION: 3'-UTR sequence of integrin beta

<400> SEQUENCE: 26
uuauuuuacc uuuuuuuuuu uucuuuaauu ccuggu                        36

<210> SEQ ID NO 27
<211> LENGTH: 19
<212> TYPE: RNA
<213> ORGANISM: Artificial Sequence
<220> FEATURE:
<223> OTHER INFORMATION: 3'-UTR sequence of CTCF

<400> SEQUENCE: 27
uuaugaaugu uauauuugu                                           19

<210> SEQ ID NO 28
<211> LENGTH: 27
<212> TYPE: RNA
<213> ORGANISM: Artificial Sequence
<220> FEATURE:
<223> OTHER INFORMATION: 3'-UTR sequence of CTCF

<400> SEQUENCE: 28
ucuuaauuuu uucucuuuuu uuucuuu                                  27

<210> SEQ ID NO 29
<211> LENGTH: 33
<212> TYPE: RNA
<213> ORGANISM: Artificial Sequence
<220> FEATURE:
<223> OTHER INFORMATION: 3'-UTR sequence of TGF beta 2

<400> SEQUENCE: 29 uuuuuuuuc cuuuuaauug uaaaugguuc uuu                            33

<210> SEQ ID NO 30
<211> LENGTH: 37
<212> TYPE: RNA
<213> ORGANISM: Artificial Sequence
<220> FEATURE:
<223> OTHER INFORMATION: 3'-UTR sequence of TGF beta 2

<400> SEQUENCE: 30
uuaaugauca uucagauugu auauauuugu uuccuuu                       37

```
<210> SEQ ID NO 31
<211> LENGTH: 25
<212> TYPE: RNA
<213> ORGANISM: Artificial Sequence
<220> FEATURE:
<223> OTHER INFORMATION: 3'-UTR sequence of TGF beta 2

<400> SEQUENCE: 31
uucaauuuuu uuuauauacu aucuu                                    25

<210> SEQ ID NO 32
<211> LENGTH: 22
<212> TYPE: RNA
<213> ORGANISM: Artificial Sequence
<220> FEATURE:
<223> OTHER INFORMATION: 3'-UTR sequence of TGF beta 2

<400> SEQUENCE: 32
uuuuucuuua auugguuuuu uu                                       22

<210> SEQ ID NO 33
<211> LENGTH: 27
<212> TYPE: RNA
<213> ORGANISM: Artificial Sequence
<220> FEATURE:
<223> OTHER INFORMATION: 3'-UTR sequence of MTP

<400> SEQUENCE: 33
ugucuugucu gagcauuuau uuucaaa                                  27

<210> SEQ ID NO 34
<211> LENGTH: 23
<212> TYPE: RNA
<213> ORGANISM: Artificial Sequence
<220> FEATURE:
<223> OTHER INFORMATION: 3'-UTR sequence of MTP

<400> SEQUENCE: 34
uucucgucuu guuuauuuua caa                                      23

<210> SEQ ID NO 35
<211> LENGTH: 32
<212> TYPE: RNA
<213> ORGANISM: Artificial Sequence
<220> FEATURE:
<223> OTHER INFORMATION: 3'-UTR sequence of MTP

<400> SEQUENCE: 35
uauaauaaua guuuauguuu uggauguuug gu                            32

<210> SEQ ID NO 36
<211> LENGTH: 27
<212> TYPE: RNA
<213> ORGANISM: Artificial Sequence
<220> FEATURE:
<223> OTHER INFORMATION: 3'-UTR sequence of cyclin D2

<400> SEQUENCE: 36
augucuuguu cuuuguguuu uuaggau                                  27

<210> SEQ ID NO 37
<211> LENGTH: 11
<212> TYPE: RNA
<213> ORGANISM: Artificial Sequence
<220> FEATURE:
<223> OTHER INFORMATION: in vitro consensus sequence
<220> FEATURE:
```

-continued

```
<221> NAME/KEY: misc_feature
<222> LOCATION: (1)..(2)
<223> OTHER INFORMATION: nn is UA or GA
<220> FEATURE:
<221> NAME/KEY: misc_feature
<222> LOCATION: (10)..(11)
<223> OTHER INFORMATION: nn is UA or AG

<400> SEQUENCE: 37
nnuuuauuun n                                                    11
```